(12) United States Patent
     Lin

(10) Patent No.: US 12,590,839 B2
(45) Date of Patent: Mar. 31, 2026

(54) SYSTEM AND METHOD FOR EMBEDDED DIFFUSE CORRELATION SPECTROSCOPY

(71) Applicant: THE RESEARCH FOUNDATION FOR THE STATE UNIVERSITY OF NEW YORK, Albany, NY (US)

(72) Inventor: Wei Lin, Stony Brook, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 406 days.

(21) Appl. No.: 18/022,793

(22) PCT Filed: Aug. 27, 2021

(86) PCT No.: PCT/US2021/047860
     § 371 (c)(1),
     (2) Date: Feb. 23, 2023

(87) PCT Pub. No.: WO2022/047101
     PCT Pub. Date: Mar. 3, 2022

(65) Prior Publication Data
     US 2023/0314221 A1     Oct. 5, 2023

Related U.S. Application Data

(60) Provisional application No. 63/071,123, filed on Aug. 27, 2020.

(51) Int. Cl.
     *G01J 3/457*     (2006.01)
     *A61B 5/00*      (2006.01)
     *A61B 5/026*     (2006.01)

(52) U.S. Cl.
     CPC ............ *G01J 3/457* (2013.01); *A61B 5/0075* (2013.01); *A61B 5/0261* (2013.01)

(58) Field of Classification Search
     CPC ... G01J 3/457; G01J 2003/284; A61B 5/0075; A61B 5/0261
     See application file for complete search history.

(56) References Cited

U.S. PATENT DOCUMENTS 5,315,562 A     5/1994  Bradley et al.
5,727,123 A     3/1998  McDonough et al.
                (Continued)

FOREIGN PATENT DOCUMENTS

CN     102798582 A     11/2012
CN     105188523 A     12/2015
               (Continued)

OTHER PUBLICATIONS

Lin et al. "Diffuse Correlation Spectroscopy Analysis Implemented on a Field Programmable Gate Array", Aug. 28, 2019, IEEE Access, vol. 7 ,2019 p. 122503-122512 (Year: 2019).*
               (Continued)

*Primary Examiner* — Stephanie E Bloss
(74) *Attorney, Agent, or Firm* — Hoffmann & Baron, LLP

(57)     ABSTRACT

DCS analyzer including a memory to store autocorrelation values, model parameters, fitting parameters, and simulated correlation values from a DCS model; a mean square error (MSE) module to compute MSE between theoretical autocorrelation values computed from the model parameters and measured autocorrelation values; a sorting module to sort three latest MSE values obtained from the MSE module and generate indexes of largest, medium, and smallest MSE values; a convergence checking module to determine whether convergence is reached in solving an autocorrelation equation; a search module to calculate $\alpha D_B$ and $\beta$ values at reflection, extension, contraction, and shrink locations; a comparison module to compare two latest MSE values and find new $\alpha D_B$ and $\beta$ values to replace values associated with a largest MSE; a state controller coupled with the memory (Continued)

and the modules to control an operation thereof; and an output buffer to present a fitted solution of the autocorrelation equation.

20 Claims, 10 Drawing Sheets

(56)  References Cited

U.S. PATENT DOCUMENTS

| | | | |
|---|---|---|---|
| 7,050,513 B1 | 5/2006 | Yakhnich | |
| 7,115,858 B1 * | 10/2006 | Holden | G01N 21/21 |
| | | | 356/369 |
| 7,372,565 B1 | 5/2008 | Holden et al. | |
| 8,082,015 B2 | 12/2011 | Yodh et al. | |
| 8,184,819 B2 | 5/2012 | Malvar et al. | |
| 10,740,884 B2 * | 8/2020 | McCall | G06T 7/62 |
| 10,775,241 B2 | 9/2020 | Hosoda et al. | |
| 10,925,525 B2 | 2/2021 | Nakaji | |
| 11,213,245 B2 | 1/2022 | Horstmeyer et al. | |
| 2003/0076875 A1 | 4/2003 | Dates | |
| 2003/0133110 A1 | 7/2003 | Tsutsui et al. | |
| 2003/0185292 A1 | 10/2003 | Fernandez-Corbaton et al. | |
| 2003/0206297 A1 | 11/2003 | Barbieri et al. | |
| 2004/0071284 A1 | 4/2004 | Abutalebi et al. | |
| 2006/0041403 A1 | 2/2006 | Jaber | |
| 2009/0122854 A1 | 5/2009 | Zhu et al. | |
| 2010/0135172 A1 | 6/2010 | Cui et al. | |
| 2010/0168586 A1 | 7/2010 | Hillman et al. | |
| 2010/0197254 A1 | 8/2010 | Yu et al. | |
| 2013/0211829 A1 | 8/2013 | Principe et al. | |
| 2013/0322638 A1 | 12/2013 | Lee et al. | |
| 2014/0126624 A1 | 5/2014 | Garmany | |
| 2014/0206980 A1 | 7/2014 | Lee et al. | |
| 2015/0098345 A1 | 4/2015 | Ekbatani et al. | |
| 2016/0345880 A1 | 12/2016 | Nakaji et al. | |
| 2016/0361017 A1 | 12/2016 | Busch, Jr. et al. | |
| 2017/0007132 A1 | 1/2017 | Zubkov et al. | |
| 2017/0048088 A1 | 2/2017 | Iqbal et al. | |
| 2018/0070830 A1 | 3/2018 | Sutin et al. | |
| 2018/0070831 A1 | 3/2018 | Sutin et al. | |
| 2018/0249911 A1 | 9/2018 | Hosoda et al. | |
| 2020/0022578 A1 | 1/2020 | Ruan et al. | |
| 2020/0333129 A1 | 10/2020 | Mohseni et al. | |
| 2020/0333130 A1 * | 10/2020 | Ruan | G01B 9/02083 |
| 2020/0333245 A1 * | 10/2020 | Mohseni | A61B 5/0066 |
| 2021/0058273 A1 | 2/2021 | Yuan et al. | |
| 2021/0338083 A1 | 11/2021 | Sie et al. | |
| 2022/0078049 A1 | 3/2022 | Yuan et al. | |

FOREIGN PATENT DOCUMENTS

| | | | | | |
|---|---|---|---|---|---|
| CN | 105266791 A | | 1/2016 | | |
| CN | 104519001 B | | 12/2017 | | |
| CN | 108768345 A | | 11/2018 | | |
| CN | 112398763 A | | 2/2021 | | |
| DE | 102 05 742 C1 | | 12/2003 | | |
| DE | 603 10 725 T2 | | 10/2007 | | |
| DE | 102020133732 A1 | | 6/2022 | | |
| EP | 1 525 726 B9 | | 4/2011 | | |
| EP | 3 094 251 A1 | | 11/2016 | | |
| EP | 3 622 882 A1 | | 3/2020 | | |
| EP | 3 827 522 A1 | | 6/2021 | | |
| EP | 4 049 373 A1 | | 8/2022 | | |
| JP | 2002-538659 A | | 11/2002 | | |
| JP | 2012-517202 A | | 7/2012 | | |
| JP | 2016-541141 A | | 12/2016 | | |
| JP | 2018-514763 A | | 6/2018 | | |
| JP | 6837990 B2 | | 3/2021 | | |
| KR | 10-0334202 B1 | | 10/2002 | | |
| KR | 10-0522340 B1 | | 10/2005 | | |
| WO | WO 00/51260 A1 | | 8/2000 | | |
| WO | WO 00/66985 A1 | | 11/2000 | | |
| WO | WO 2009/050434 A2 | | 4/2009 | | |
| WO | WO 2010/028351 A2 | | 3/2010 | | |
| WO | WO 2017/037623 A2 | | 3/2017 | | |
| WO | WO 2017/147539 A1 | | 8/2017 | | |
| WO | WO 2018/090040 A1 | | 5/2018 | | |
| WO | WO 2019/245533 A1 | | 12/2019 | | |
| WO | WO-2020197493 A1 * | | 10/2020 | | A61B 5/026 |
| WO | WO 2021/080566 A1 | | 4/2021 | | |

OTHER PUBLICATIONS

Stapels et al. "A scalable correlator for multichannel diffuse correlation spectroscopy", 2016, Proceedings vol. 9698, Advanced Biomedical and Clinical Diagnostic and Surgical Guidance Systems XIV; 969816 (2016) (Year: 2016).*

Lin, Wei, "Diffuse Correlation Spectroscopy Analysis Implemented on a Field Programmable Gate Array", IEEE Access, 2019; 7: 122503-1225122, Aug. 28, 2019.

Boas, D. A., et al., "Spatially varying dynamical properties of turbid media probed with diffusing temporal light correlation," J. Opt. Soc. Amer. A, Opt. Image Sci., vol. 14, No. 1, pp. 192-215, 1997.

Durduran, T., et al., "Diffuse Optics for Tissue Monitoring and Tomography," Rep. Prog. Phys., vol. 73, No. 7, Jul. 2010, Art. No. 076701.

Cortese, L., et al., "Liquid Phantoms for Near-Infrared and Diffuse Correlation Spectroscopies with Tunable Optical and Dynamic Properties," Biomed. Opt. Express, vol. 9, No. 5, pp. 2068-2080, 2018.

* cited by examiner $\beta = 0.500$
$\alpha D_B = 7.33 \times 10^{-10}$ $\beta = 0.468$
$\alpha D_B = 5.44 \times 10^{-10}$

SYSTEM AND METHOD FOR EMBEDDED DIFFUSE CORRELATION SPECTROSCOPY

CROSS-REFERENCE TO RELATED APPLICATIONS

This application is the U.S. National Phase of PCT/US2021/047860, filed on Aug. 27, 2021, and claims the benefit of U.S. Provisional Patent Application No. 63/071,123, filed on Aug. 27, 2020, entitled "System and Method for Embedded Diffuse Correlation Spectroscopy," the disclosures of which are incorporated by reference herein in their entities for all purposes.

STATEMENT OF GOVERNMENT RIGHTS

This invention was made with government support under contract number U01NS095761 awarded by the National Institutes of Health. The government has certain rights in the invention.

BACKGROUND

Field

The present invention relates generally to the electrical, electronic and computer arts, and, more particularly, to a system and method for embedded diffuse correlation spectroscopy.

Related Art

Diffuse correlation spectroscopy (DCS) is an emerging optical technique capable of measuring blood flow in biological tissue using multiply scattered light and has widely been applied to quantify blood perfusion in tissue in vivo. The light source used in DCS is typically a long coherence length laser, which is delivered to a medium of interest through a large-core optical fiber while the back-scattered (i.e., reflected) intensity is collected using a small-core (single mode) fiber, placed at a fixed distance (the source-detector separation SDS) from the center of the source fiber. The detected signal is transmitted to a photon counter that in turn is electronically coupled to a hardware correlator board.

In a DCS measurement, temporal changes in the interference pattern of light, which has passed through tissue, are quantified by an autocorrelation function. This autocorrelation function is further parameterized through a non-linear curve fit to a solution to the diffusion equation for coherence transport. However, the computational load associated with this non-linear curve fitting is a barrier for deployment of DCS for clinical use, where real-time results, as well as instrument size and simplicity, are important considerations.

SUMMARY

Principles of the present invention, as manifested in one or more embodiments thereof, are directed to an embedded diffuse correlation spectroscopy (DCS) apparatus and methods configured to mitigate the computational bottleneck associated with non-linear curve fitting of the DCS autocorrelation function, which is preferably achieved through the development of specific hardware modules for implementing correlator and analyzer functionality of the DCS.

In one or more embodiments, an example embedded DCS apparatus includes hardware correlator and analyzer modules. The correlator module is configured to process photon pulses from a photo detector and to generate an autocorrelation of the light intensity in real-time. The analyzer module implements a DCS curving fitting algorithm on digital logic circuitry. Both hardware modules can be implemented and tested on a field programmable gate array (FPGA) chip, although embodiments of the invention are not limited to an FPGA, but rather contemplate that the correlator and analyzer modules may be implemented in other hardware as well, such as, for example, an application-specific integrated circuit (ASIC). A hardware solution is more efficient than a typical software solution for the correlation and analysis. The hardware modules can be duplicated for processing multiple channels of DCS data in real-time. The DCS apparatus and methods according to aspects of the invention described herein demonstrate a utility of this analyzer in pre-clinical large animal studies of spinal cord ischemia. Embodiments of the invention are well-suited for any DCS applications, particularly those demanding mobility and real-time processing.

In accordance with an embodiment of the invention, an embedded DCS analyzer includes a memory for storing autocorrelation values, model parameters used in solving an autocorrelation equation of scattered light, fitting parameters and simulated correlation values obtained from a theoretical DCS model, and a hardware mean square error (MSE) module configured to compute MSE between theoretical autocorrelation values computed from the model parameters and measured autocorrelation values. The analyzer further includes a hardware sorting module configured to sort a latest three MSE values obtained from the MSE module and to generate indexes of largest, medium, and smallest MSE values, and a hardware convergence checking module configured to determine whether convergence is reached in fitting the autocorrelation equation. A hardware search module is included in the analyzer, configured to calculate $\alpha D_B$ and $\beta$ values at reflection, extension, contraction and shrink locations, the $\alpha D_B$ and $\beta$ values being calculated in parallel. A hardware comparison module is configured to compare two latest MSE values and to find new $\alpha D_B$ and $\beta$ values to replace those values associated with a largest MSE. A state controller is coupled with the memory, the MSE module, the sorting module, the convergence checking module, the search module, and the comparison module for controlling an operation thereof, and an output buffer is included for presenting, as an output of the DCS analyzer, a fitted solution of the autocorrelation equation.

In accordance with another embodiment of the invention, an apparatus for performing DCS includes a hardware DCS correlator and a hardware DCS analyzer coupled with the DCS correlator and embedded therewith on the same integrated circuit chip. The DCS analyzer includes a memory for storing autocorrelation values, model parameters used in solving an autocorrelation equation of scattered light, fitting parameters and simulated correlation values obtained from a theoretical DCS model, and a hardware mean square error (MSE) module configured to compute MSE between theoretical autocorrelation values computed from the model parameters and measured autocorrelation values. The analyzer further includes a hardware sorting module configured to sort a latest three MSE values obtained from the MSE module and to generate indexes of largest, medium, and smallest MSE values, and a hardware convergence checking module configured to determine whether convergence is reached in fitting the autocorrelation equation. A hardware search module is included in the analyzer, configured to calculate $\alpha D_B$ and $\beta$ values at reflection, extension, contraction and shrink locations, the $\alpha D_B$ and $\beta$ values being

3

4 calculated in parallel. A hardware comparison module is configured to compare two latest MSE values and to facilitate a state controller to find new $\alpha D_B$ and $\beta$ values to replace those values associated with a largest MSE. The state controller is coupled with the memory, the MSE module, the sorting module, the convergence checking module, the search module, and the comparison module for controlling an operation thereof, and an output buffer is included for presenting, as an output of the DCS analyzer, a fitted solution of the autocorrelation equation.

In accordance with yet another embodiment of the invention, a multi-tau DCS correlator for processing dynamic light-scattering data is provided. The DCS correlator includes a single 8-channel hardware correlator, a single multi-tau data combiner operatively coupled with the 8-channel hardware correlator, memory coupled with the 8-channel hardware correlator, the memory being configured to compute correlation values in multiples of eight, and a hardware controller configured to modify a total number of iterations of the DCS correlator to thereby generate a required correlation result.

As the term may be used herein, "facilitating" an action contemplates performing the action, making the action easier, helping to carry out the action, or causing the action to be performed. Thus, by way of example only and without limitation, in the context of a processor-implemented method, instructions executing on one processor might facilitate an action carried out by instructions executing on a remote processor, by sending appropriate data or commands to cause or aid the action to be performed. For the avoidance of doubt, where an actor facilitates an action by other than directly performing the action itself, it is assumed that the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform example method steps.

Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. By way of example only and without limitation, a DCS system and method according to one or more embodiments of the invention may provide one or more of the following features, among other advantages:

reduces the computational bottleneck associated with non-linear curve fitting of the DCS autocorrelation function;

hardware implementation of DCS analyzer significantly increases the speed of non-linear curve fitting and enables real-time calculation of blood flow index (BFI);

correlator and analyzer modules can be duplicated for processing multiple channels of DCS data in real-time; and allows integration of DCS correlator and analyzer functionality on the same chip, thereby significantly reducing the size of the DCS system for portability.

These and other features and advantages of the present invention will become apparent from the following detailed description of illustrative embodiments thereof, which is to be read in connection with the accompanying drawings.

BRIEF DESCRIPTION OF THE DRAWINGS

Non-limiting and non-exhaustive embodiments of the present invention will be described with reference to the following drawings which are presented by way of example only, wherein like reference numerals (when used) indicate corresponding elements throughout the several views unless otherwise specified, and wherein.

Figure 1:
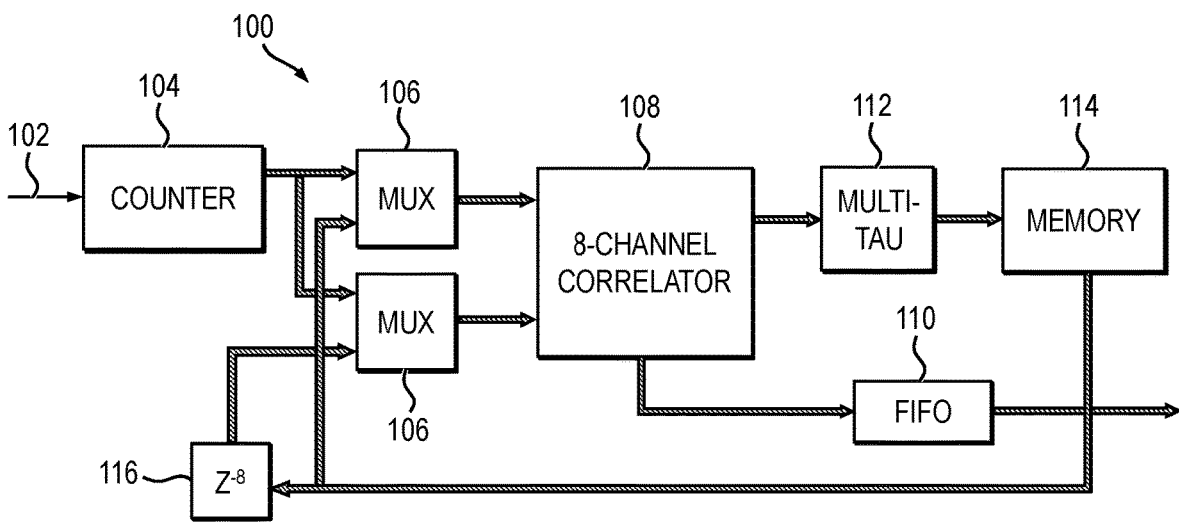
FIG. 1 is a block diagram depicting the architecture of at least a portion of an example correlator for use in a DCS system, according to one or more embodiments of the present invention.

It is to be appreciated that elements in the figures are illustrated for simplicity and clarity. Common but well-understood elements that may be useful or necessary in a commercially feasible embodiment may not be shown in order to facilitate a less hindered view of the illustrated embodiments.

DETAILED DESCRIPTION

Principles of the present invention, as manifested in one or more embodiments thereof, will be described herein in the context of an illustrative embedded diffuse correlation spectroscopy (DCS) system, apparatus and/or methods. It is to be appreciated, however, that the invention is not limited to the specific system, apparatus and/or methods illustratively shown and described herein. Rather, it will become apparent to those skilled in the art given the teachings herein that numerous modifications can be made to the embodiments shown that are within the scope of the claimed invention. That is, no limitations with respect to the embodiments shown and described herein are intended or should be inferred.

As previously stated, DCS measurements involve quantifying temporal changes in the interference pattern of light, which has passed through tissue, using an autocorrelation function. This autocorrelation function is further parameterized through a non-linear curve fit to a solution to the diffusion equation for coherence transport. Unfortunately, the significant computational load associated with this non-linear curve fitting is an impediment for deployment of standard DCS systems in a clinical application where real-time results, as well as instrument size and simplicity, are critical factors.

Aspects of the present invention, as manifested in one or more embodiments thereof, advantageously provide an embedded DCS system and methods configured to reduce the computational bottleneck associated with non-linear curve fitting of the DCS autocorrelation function, which is primarily achieved through the development of specific embedded hardware modules for implementing correlator and analyzer functionality in the DCS system. This hardware solution is more efficient than a typical software solution for the correlation and analysis. The correlator and analyzer modules can be duplicated, in one or more embodiments, for processing multiple channels of DCS data in real-time. By way of example only and without limitation, the DCS apparatus and methods according to embodiments of the invention described herein demonstrate the utility of this analyzer in pre-clinical large animal studies of spinal cord ischemia, although principles of the invention are not limited to this specific example. Rather, these embedded hardware modules are well-suited for any DCS applications demanding increased portability and real-time processing.

DCS is a relatively new optical technology to probe microvascular blood flow. In a typical implementation, the tissue of interest is illuminated with a long-coherence length near infra-red (NIR) laser and the temporal fluctuation of optical interference patterns formed on the tissue surface are detected. This interference ("speckle") pattern fluctuates on a time scale dependent on the motion of "scatterers" in tissue dominated by red blood cells. Such temporal fluctuations can be quantified with an autocorrelation function. A correlation diffusion equation (see, e.g., D. A. Boas and A. G. Yodh, "Spatially varying dynamical properties of turbid media probed with diffusing temporal light correlation," *J. Opt. Soc. Amer. A, Opt. Image Sci., Vol.* 14, No. 1, pp. 192-215, 1997) relates tissue optical properties and motion of scatterers to the correlation decay.

By fitting the measured autocorrelation curve using the theoretical model to the diffusion correlation function, a blood flow index (BFI) can be derived. This technology has been validated against various techniques, including magnetic resonance imaging (MRI), microspheres, and Doppler ultrasound. It is fundamentally different from measurements of blood volume and/or saturation with diffuse optical spectroscopy (DOS) or near infrared spectroscopy (NIRS) devices. DCS probes the motion of scatterers (including red blood cells) in tissue on scales of about 1 microsecond (p), quantifying this motion every 10-1000 milliseconds (ms), while DOS/NIRS techniques are only capable of measuring tissue absorption and scattering at significantly greater than 1 ms time scales, which is unacceptable for real-time processing.

DCS has been widely used to assess blood flow in tissues more than 1 centimeter (cm) below the tissue surface, permitting noninvasive assessment of blood flow. This technique is particularly useful to measure microvascular cerebral blood flow and offers some unique advantages over other techniques.

For example, DCS has been widely applied to measure cerebral blood flow in the critically and chronically ill, including adults with ischemic stroke or during neuro-critical care, and pediatric patients. This technology has also been applied to cancer monitoring, as many tumors have abnormal microvasculature and enhanced blood flow. Recently, minimally invasive DCS probes have been developed to allow for measurement of spinal cord blood flow. These probes can be placed into the spinal canal within the epidural space through a laminotomy or percutaneously via an epidural needle to monitor spinal cord blood flow. Extensive studies in large animal models have demonstrated the feasibility of these measurements during a variety of surgical interventions. Monitoring spinal cord ischemia may have utility during aortic surgery, spine reconstruction procedures, and in the management of patients after spinal cord injury to prevent secondary ischemia. Recently, so-called "Fast DCS" has been developed which measures blood flow dynamics at up to 100 Hz utilizing a software correlator. This higher temporal resolution enables resolution of blood flow pulsation due to the cardiac cycle.

The DCS data analysis typically requires two steps: (1) calculating a temporal autocorrelation function of the scattered light intensity, and (2) fitting the measured autocorrelation to a theoretical model, i.e. a solution of the correlation diffusion equation, to extract a blood flow index. The autocorrelation function measured in DCS requires a large range of correlation delay times ($\tau$: 200 ns-1 ms). In calculating the temporal autocorrelation function in DCS, a "multi-tau" approach, which adjusts integration times as $\tau$ increases, is generally used to improve computational efficiency by significantly reducing the number of correlation values to be calculated. Multi-tau correlation has been implemented in software and in hardware using FPGA technology.

Both traditional and fast DCS measurements require a non-linear fit of the autocorrelation curve at each time point of measurement to a solution of the correlation diffusion equation. This forms a computational bottleneck, as these fitting algorithms require significant computation resources. This fit is frequently performed in post-processing, reducing the utility of DCS measurements, e.g., in guiding surgical interventions in real time.

Advantageously, aspects of the invention provide a hardware correlator module, configured to process photon pulses from a photo detector and generate an autocorrelation of the light intensity in real-time, and a hardware analyzer that implements the DCS curve-fitting algorithm on digital logic circuitry. In one or more embodiments, the correlator and analyzer modules are implemented and tested on an FPGA, for example on a Xilinx FPGA, with significantly increased processing efficiency. The modules may also be implemented in an ASIC or other hardware. Coupled with previous work utilizing FPGAs to calculate the correlation function, this has beneficially opened the path to integrate the entire data processing necessary for implementing DCS on a single silicon chip.

FIG. 1 is a block diagram depicting the architecture of at least a portion of an example correlator 100, according to one or more embodiments of the invention. The correlator 100 follows a multiple tau digital correlation scheme in which digital pulses 102 from a photodetector are supplied as an input to a counter 104. The counter 104 counts the number of pulses within a prescribed window of time (e.g., about 200 ns). The number of count values is predetermined. The data stream is split into two identical copies that are selected by multiplexers 106 coupled with the counter 104 and sent to an 8-channel correlator 108 for autocorrelation. The 8-channel correlator 108 takes two streams of data and produces eight correlation values with delays from $\Delta\tau$ to $8\Delta\tau$, where $\Delta\tau$ is the unit correlation lag time. Its initial value is the time window of the counter 104. Since both inputs are from the same data set, the output is the autocorrelation. The correlation data are output through a first-in-first-out (FIFO) buffer 110.

The correlator 108 also sends the counter values at its input to a multi-tau module 112 configured to combine the values of two consecutive values to create a new counter window with double the window size. In one or more embodiments, module 112 preferably has a bypass switch that will disable the value combination. The bypass switch is active during the first iteration when the data is originated from the counter 104. The switch becomes inactive in the following iterations to enable combining values when the data is obtained from the memory via multiplexers 106. Data from the multi-tau module 112 are then stored in a memory 114. After the predetermined number of count values from the counter 104 are processed, the multiplexers 106 select the data from the memory for the next iteration. The data stream read from the memory 114 is split into two identical copies, with one of the copies being passed through an $8\Delta\tau$ delay unit 116 ($Z^{-8}$) before being supplied to one of the multiplexers 106 and the other copy being supplied directly to the other multiplexer 106. Therefore, the correlation output will have the delays of $9\Delta\tau$ to $16\Delta\tau$ as defined in the multi-tau correlation scheme during the second iteration. The correlation output during the third iteration will have the delays of $18\Delta\tau$ to $32\Delta\tau$ with $2\Delta\tau$ as the time step. Subsequent iterations will have eight correlation values with the time step doubled from the next previous iteration. The number of iterations is determined by the number of requested correlation values, which in this example is eight times the number of iterations.

Figure 2:
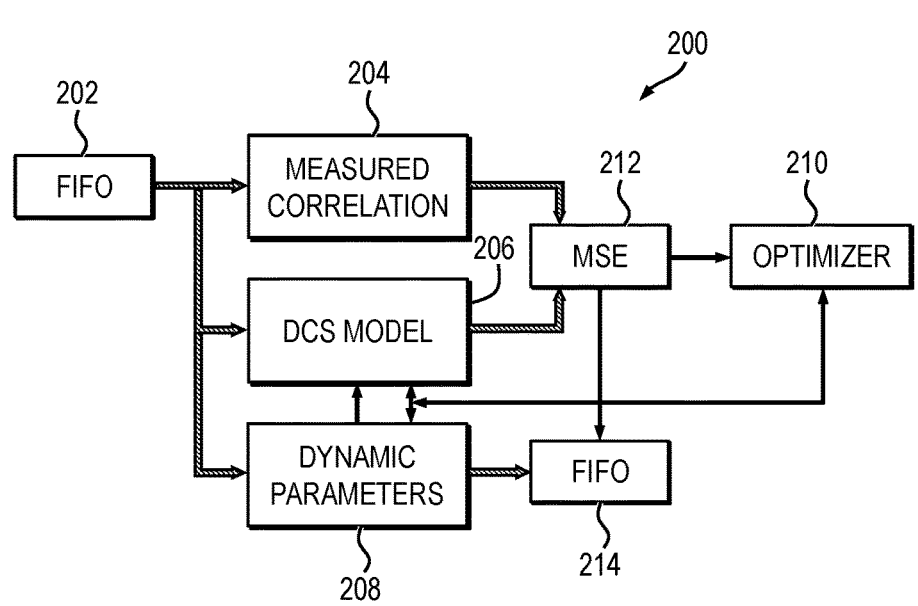
FIG. 2 is a block diagram depicting the architecture of at least a portion of an example analyzer for use in a DCS system, according to one or more embodiments of the present invention.

FIG. 2 is a block diagram depicting the architecture of at least a portion of an example analyzer 200, according to one or more embodiments of the invention. With reference to FIG. 2, data from the correlator (e.g., correlator 100 of FIG. 1) is the autocorrelation of the scattered light received by the photodetector. This data is sent to an analyzer through a FIFO buffer 202 and stored in a memory for measured correlation 204. A DCS model 206 included in the analyzer 200 is a hardware module configured to compute the same autocorrelation from a theoretical model. It also receives constant parameters of the theoretical DCS model through the FIFO buffer 202 and stored them in the memory for measured correlation 204. Those parameters include a light absorption coefficient, scattering coefficient and a separation of the source detector. Dynamic parameters, $\beta$ and $\alpha D_B$, used in the DCS analysis are preferably stored in a separate dynamic parameters memory 208.

A Nelder-Mead algorithm is preferably used for fitting of the theoretical autocorrelation with the measured autocorrelation by adjusting the dynamic parameters $\beta$ and $\alpha D_B$. The DCS model 206 starts the computation using initial values of $\beta$ and $\alpha D_B$ to generate the theoretical autocorrelation, which is compared with the measured autocorrelation. The Nelder-Mead algorithm requires three pairs of $\beta$ and $\alpha D_B$ values at any given time. An optimizer 210 checks the mean square errors (MSEs) calculated by an MSE module 212 from the three pairs of $\beta$ and $\alpha D_B$ values and generates new $\beta$ and $\alpha D_B$ values to replace the $\beta$ and $\alpha D_B$ existing values that have the largest MSE values in the dynamic parameters memory 208. The iteration continues until the improvement of the $\beta$ and $\alpha D_B$ values are within a prescribed range; e.g., within the relative change of $10^{-5}$. At this point, the $\beta$ and $\alpha D_B$ values related to the minimum MSE is output through a second FIFO buffer 214. The value of $\alpha D_B$ is proportional to the BFI.

In one or more embodiments, a simplest (infinite homogeneous medium, equation (1) below) and most common (semi-infinite half-space, equation (2) below) analytical solutions are applied to the diffuse correlation equation. In the semi-infinite half-space (eqn. 2), there is a planar boundary between a homogenous diffuse media and a non-diffuse medium (e.g., tissue-air) at z=0 in the solutions described in T. Durduran et al., "Diffuse Optics for Tissue Monitoring and Tomography," *Rep. Prog. Phys., Vol.* 73, No. 7, June 2010, Art. No. 076701. For the purposes of these calculations, tissue optical properties (e.g., index of refraction, absorption, and scattering) and experimental geometry (e.g., source-detector separation) are assumed constants in the fitting procedure. Combinations of these constants are designated as A, B, F and H in equations (1) and (2). The resulting simplified equations have only two free parameters: $\beta$ and $\alpha D_B$, which are iteration parameters.

$$g_2(r, \tau) = 1 + \beta \left| \frac{e^{-r\sqrt{A+B\alpha D_B\tau}}}{F} \right|^2 \qquad (1)$$

$$g_2(\rho, 0, \tau) = 1 + \beta \left| \frac{e^{-r_1\sqrt{A+B\alpha D_B\tau}}}{r_1 H} - \frac{e^{-r_b\sqrt{A+B\alpha D_B\tau}}}{r_b H} \right|^2 \qquad (2)$$

In equations (1) and (2) above, $\beta$ is the inverse of the number of detected modes. In one or more embodiments, $\beta \leq \frac{1}{2}$ is assumed, since unpolarized light is being detected through a single mode fiber. In an ideal experiment in which there is only a single spatial and polarization mode detected, $\beta = 1$. As the device according to one or more embodiments of the invention does not select the polarization of the highly scattered detected light with two polarization modes, $\beta$ is $\frac{1}{2}$. Any additional modes, background light, etc., will further reduce this value. Clinical experiments often take place under non-ideal circumstances and $\beta$ may change with time and is a parameter in experimental data fitting. The product $\alpha D_B$ is often termed the "blood flow index" (BFI).

The DCS analysis computes $\alpha D_B$ and $\beta$ values through a best fit of the theoretical autocorrelation function from equation (1) or (2) to the acquired experimental intensity autocorrelation $g_{2e}(\tau)$. The mean square error (MSE) of the fit is defined using equation (3) below, where N is the number of values in $g_{2e}(\tau)$. The best fit criteria is defined as the minimum of the MSE.

$$MSE = \frac{1}{N}\sum_1^N (g_2(\tau_i) - g_{2e}(\tau_i))^2 \qquad (3)$$

In one or more embodiments, an iterative, non-linear Nelder-Mead method is used to search the minimum value of MSE without the need to calculate its derivative. In one or more embodiments, the algorithm is implemented using an FPGA for true hardware computing.

An FPGA chip, such as those available from Xilinx, Altera, Actel, Lattice and other semiconductor companies, has a large number of configurable logic blocks (CLB), digital signal processing (DSP) slices, and distributed memory integrated on one silicon chip. FPGA hardware computing employs a parallel processing technology and implements algorithms in hardware as digital logic circuits using a combination of the CLBs, DSP slices and memory blocks on the FPGA chip. Compared with software solutions for the same computation, an FPGA implementation eliminates the necessity for an operating system and guarantees higher throughput. Algorithms implemented on an FPGA can be performed much faster than those programs in a typical computer language because the performance of the FPGA is not compromised by the overhead of operating systems and other unrelated processes running in the background.

Numeric representation is the key factor that determines the complexity of the computing logic. Fixed-point representation was popular in the past when the FPGA resources were not abundant. Its limited resolution can introduce significant computing error that could alter the convergence of the algorithm. Furthermore, the dynamic range of fixed-point value is also limited and can easily cause overflow during computation. The term $\alpha D_B$ is roughly $10^{-8}$ smaller than $\beta$ in the DCS model, and thus floating-point representation is a better choice than fixed point. As the FPGA resources grow exponentially with technology development, it becomes more affordable to adopt floating-point representation in the FPGA to address the issues in fixed-point representation.

There are two floating-point representations: single floating-point representation that uses 32-bit binary and double precision representation that uses 64-bit binary. Both are defined by the IEEE Standard for Binary Floating Point Arithmetic (IEEE 754). A single floating-point representation is adopted in the DCS analyzer, in one or more embodiments, because it consumes a moderate amount of DSP slices and logic cells and offers reasonable resolution and dynamic range. In other embodiments, double precision can be used, particularly if the FPGA resources are sufficient to hold the computation logic of the double precision operations of the algorithm. The FPGA can also accommodate the customized floating point data type for the optimal use of the FPGA resources. However, an extra step of conversion to either single precision or double precision data type is required for subsequent processing of the FPGA.

It is challenging to build the computing circuits of arithmetic operations and math functions from scratch. Fortunately, FPGA manufacturers have provided a solution by offering FPGA IP cores for the hardware computation. For example, Xilinx (Xilinx, Inc., San Jose, CA) offers IP cores that adopted the CORDIC (COordinate Rotation DIgital Computer) algorithm, also known as Volder's algorithm, and expanded the support to cover the basic math functions of trigonometric, exponential and logarithmic functions. Those IP cores support the computation in both single precision and double precision format as well as customized floating-point representation.

A "pipeline" is the primary structure for high throughput parallel processing in an FPGA. It divides an algorithm into multiple steps and each step is implemented as a digital module in the FPGA, which completes its operation within one FPGA clock cycle. The modules in the pipeline work simultaneously under the same FPGA clock signal, which is a series of digital pulses of fixed frequency. The signal edge (e.g., rising edge) moves the data one step forward in the pipeline. Therefore, the pipeline inputs data one per FPGA clock and outputs the processed data one per FPGA clock after a fixed latency (see equation (4) below). Computing cores are designed as the pipelines and can be connected in serial to form a larger pipeline. If M is the number of clocks to process the first data point through the pipeline and $\Delta T$ is the clock cycle, then $M \cdot \Delta T$ will be the time delay or latency of the FPGA computation pipeline. The total time, T, needed for processing N data points in a pipeline can be determined using the following equation:

$$T = (M+N-1)\Delta T \qquad (4)$$

Data synchronization is an essential mechanism to ensure the correct data flow in the pipeline. If the operands at the inputs of a core are from different data paths, they must be synchronized to guarantee the correct output. This is achievable by adjusting the delays in the data flow paths to synchronize the input data.

Figures 3, 4:
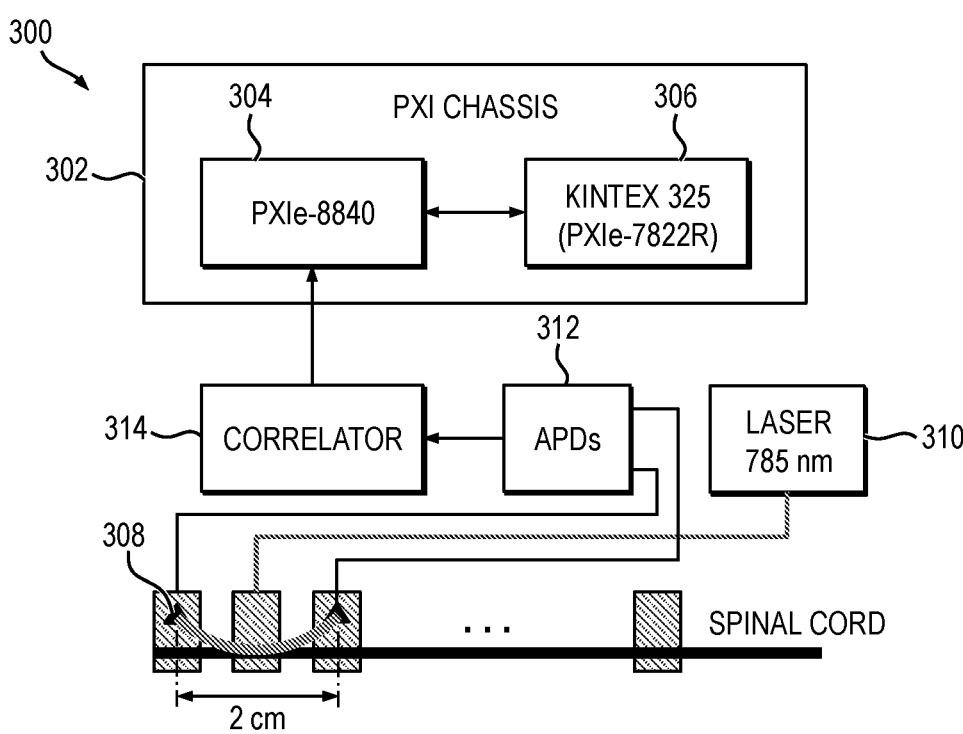
FIG. 3 is a block diagram depicting at least a portion of an example DCS system including a hardware-implemented (e.g., field programmable gate array (FPGA)) analyzer, according to one or more embodiments of the present invention.
FIG. 4 depicts an example probe suitable for use in conjunction with the illustrative DCS system shown in FIG. 3, according to one or more embodiments of the present invention.

By way of example only and without limitation or loss of generality, FIG. 3 is a block diagram depicting at least a portion of an example DCS system 300 including an FPGA analyzer, according to one or more embodiments of the invention. In an example application, the DCS system 300 was used in the preclinical study of spinal cord ischemia during spinal cord distraction in an adult sheep model. The DCS system 300 includes a computer 302 implemented as a PXI embedded computer system running Windows 7 (Microsoft Corp., Redman, WA) or other operating system. The computer 302 includes an embedded controller 304, such as, for example, a National Instruments PXIe-8840 (National Instruments, Austin, TX) with a reconfigurable digital I/O PXIe module 306 power by, for example, Xilinx Kintex 325 (PXIe-7822R, National Instruments, Austin, TX).

A plurality of fiber optic probes 308 are used to convey light supplied by a light source and to return scattered light from tissue to be detected (e.g., spinal cord tissue). FIG. 4 depicts an example probe 400 suitable for use with the illustrative DCS system 300 shown in FIG. 3, according to one or more embodiments of the invention. In this illustrative embodiment, the probe 400 includes a pair of single-mode detector fibers 402 placed symmetrically about a source fiber 404, with the source and detector fibers encased in a cylindrical sheath 406, which may include a milky plastic encapsulation material.

With continued reference to FIG. 3, a long coherence laser 310, such as, for example, a 785 nm laser (e.g., manufactured by Crystalaser of Reno, NV), is coupled into the source fiber (e.g., 404 in FIG. 4) of a corresponding probe 308 and attenuated to about 25 milliwatts (mW). Each detector fiber (e.g., 402 in FIG. 4) in the probe 308 is connected to an individual avalanche photodetector (APD) 312. The scattered light from tissue (e.g., spinal tissue) is collected by the fiber optic probe 308 and a corresponding silicon APD (e.g., model SPCM-AQ4C, Excelitus Technologies, Watertown, MA) converts the photons into a series of electronic pulses.

A correlator 314 included in the DCS system 300 is coupled to the controller 304 in the computer 302. The correlator 314 is configured to count the pulses, representing photons, received from the APDs 312 and to output an autocorrelation function, which is supplied to the controller 304. The correlation data are transferred to the embedded computer 302 through a Universal Serial Bus (USB) or other communication connection (either wired or wireless).

In one or more embodiments, a semi-infinite medium model solution to the correlation diffusion equation is used to derive the BFI at each time point. In a preparatory step, some constant values are preferably combined to avoid redundant computation and conserve FPGA resources. The values of the terms $1/(r_1 \cdot H)$ and $1/(r_b \cdot H)$ are preferably calculated beforehand so that multiplication replaces division (which is a more difficult operation to implement in digital logic) in equation (2) above. The product of $B \cdot \tau$ is also calculated in advance, where r is a series of time delays corresponding to the correlation values. In addition, one is subtracted from the acquired correlation values to thereby eliminate the need to implement a "plus one" operation in equation (2) for the MSE calculation in equation (3). The modified correlation values and the corresponding product of $B \cdot \tau$ are sent to the FPGA via a first-in-first-out (FIFO) buffer and stored in two memory blocks in the FPGA memory, as will be described in further detail herein below in conjunction with FIG. 5. The initial values of $\alpha D_B$ and $\beta$ and the model constants are sent to the FPGA and stored in registers in the FPGA memory for easy access.

Figure 5:
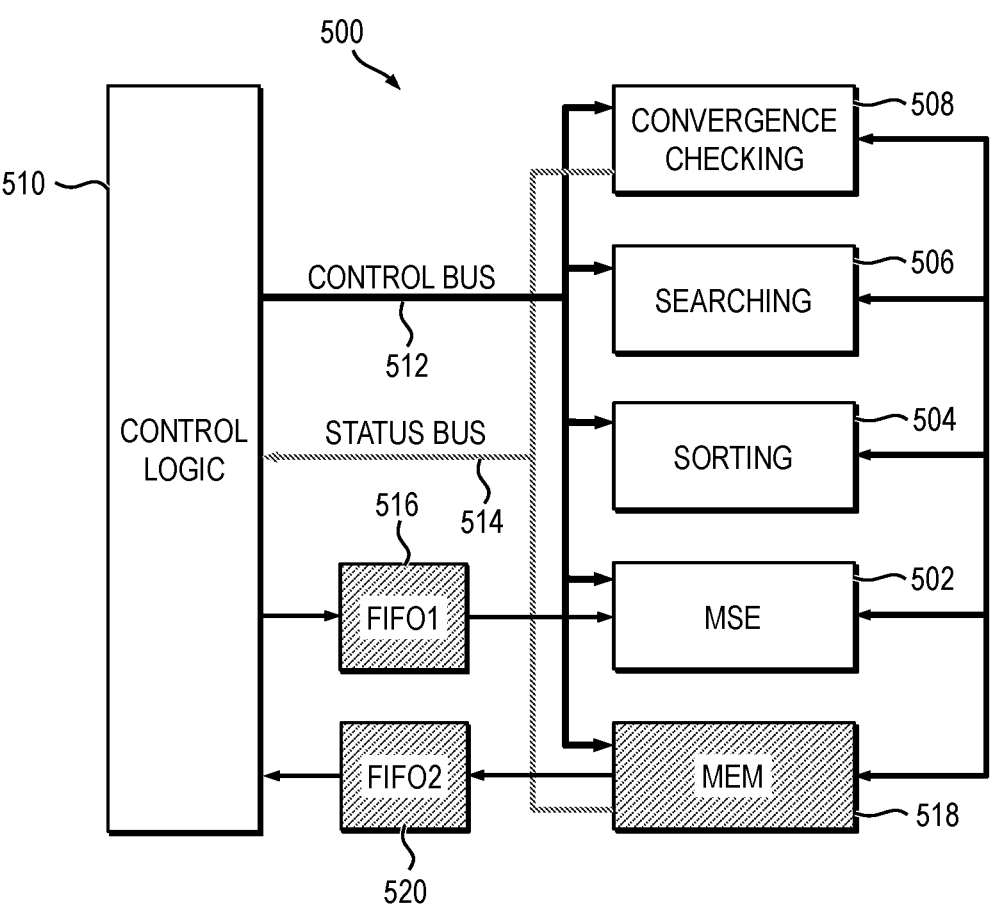
FIG. 5 is a block diagram depicting at least a portion of example computing logic including multiple pipelines for implementing a Nelder-Mead method of numerical modeling in the embedded DCS system, according to one or more embodiments of the present invention.

FIG. 5 is a block diagram depicting at least a portion of example computing logic 500 including multiple modules for implementing a Nelder-Mead method of numerical modeling in the embedded DCS system (e.g., DCS system 300 shown in FIG. 3), according to one or more embodiments of the invention. By changing one or more parameters to the computing logic 500, the computing logic can beneficially implement both semi-infinite and infinite medium model solutions to the correlation diffusion equation for deriving the BFI. In one or more embodiments, the computations performed in the Nelder-Mead algorithm are divided into four components, each of which are implemented using a separate pipeline. As shown in FIG. 5, the computing logic 500 includes an MSE module 502 configured to calculate the MSE of each $\alpha D_B$ and $\beta$ pair, a sorting module 504 configured to find a sequence of the latest three MSEs, a searching module 506 configured to find new pair of $\alpha D_B$ and $\beta$ values that have a smaller MSE, and a convergence module 308 configured to determine when to terminate the curve fitting.

With continued reference to FIG. 5, the computing logic 500 includes control logic 510, or other controller (e.g., state controller), coupled with the MSE, sorting, searching and convergence modules 502-508 via a control bus 512 and a status bus 514. The control logic 510 receives the status of the modules 502-508 from the status bus 514 and uses rules in accordance with the Nelder-Mead algorithm to determine an operation sequence of the modules, which is controlled via the control bus 512. As previously stated, modified correlation values and the corresponding product of $\tau_n$ generated by the control logic 510 are sent to the FPGA via a first FIFO buffer 516 (FIFO1), or other storage element, and stored in respective memory blocks in an FPGA memory 518 (MEM). Paths between the memory 518 and the four modules 502-508 are preferably bidirectional for data transmission.

The following is a non-limiting description of the general flow of the sequence control, according to one or more illustrative embodiments. First, the control logic 510 starts the MSE module 502 to calculate the MSE of three pairs of $\alpha D_B$ and $\beta$ values. The MSEs are then stored in the memory 518 for future use. Second, the control logic 510 sends the three MSEs to the sorting module 504 to rank the MSEs. The output data of the sorting module 504 are the indexes of $\alpha D_B$ and $\beta$ pairs corresponding to the sorted MSEs and are preferably stored in registers for the convergence module 508 and the searching module 506. Third, the control logic 510 selects the smallest and largest MSE and sends them to the convergence module 508 to test if a difference between the two values is within a prescribed range.

If the convergence criterion is met, the control logic 510 outputs $\alpha D_B$ and $\beta$ values of the smallest MSE via a second FIFO buffer 520 (FIFO2), or other storage element. Otherwise, the control logic 510 starts the searching module 506 using $\alpha D_B$ and $\beta$ pairs of the two smallest MSEs to find candidates of the new pairs with the reflection, extension and contraction formulae defined in the algorithm. The MSEs of those candidates of $\alpha D_B$ and $\beta$ pairs are computed using the MSE module 502 again, and the new $\alpha D_B$ and $\beta$ pair is selected by the control logic 510 so that its MSE is at least smaller than the largest MSE calculated in the previous step. The new $\alpha D_B$ and $\beta$ pair will replace that of the largest MSE.

If the searching module 506 fails to find the new $\alpha D_B$ and $\beta$ pair, the searching module will generate two pairs of $\alpha D_B$ and $\beta$ values using a shrink formula in the algorithm. The control logic 510 replaces the $\alpha D_B$ and $\beta$ pairs of two largest MSEs with the two new $\alpha D_B$ and $\beta$ pairs and computes their MSEs using the MSE module 502. The iteration repeats from the second step until the convergence criteria are satisfied.

Figure 6:
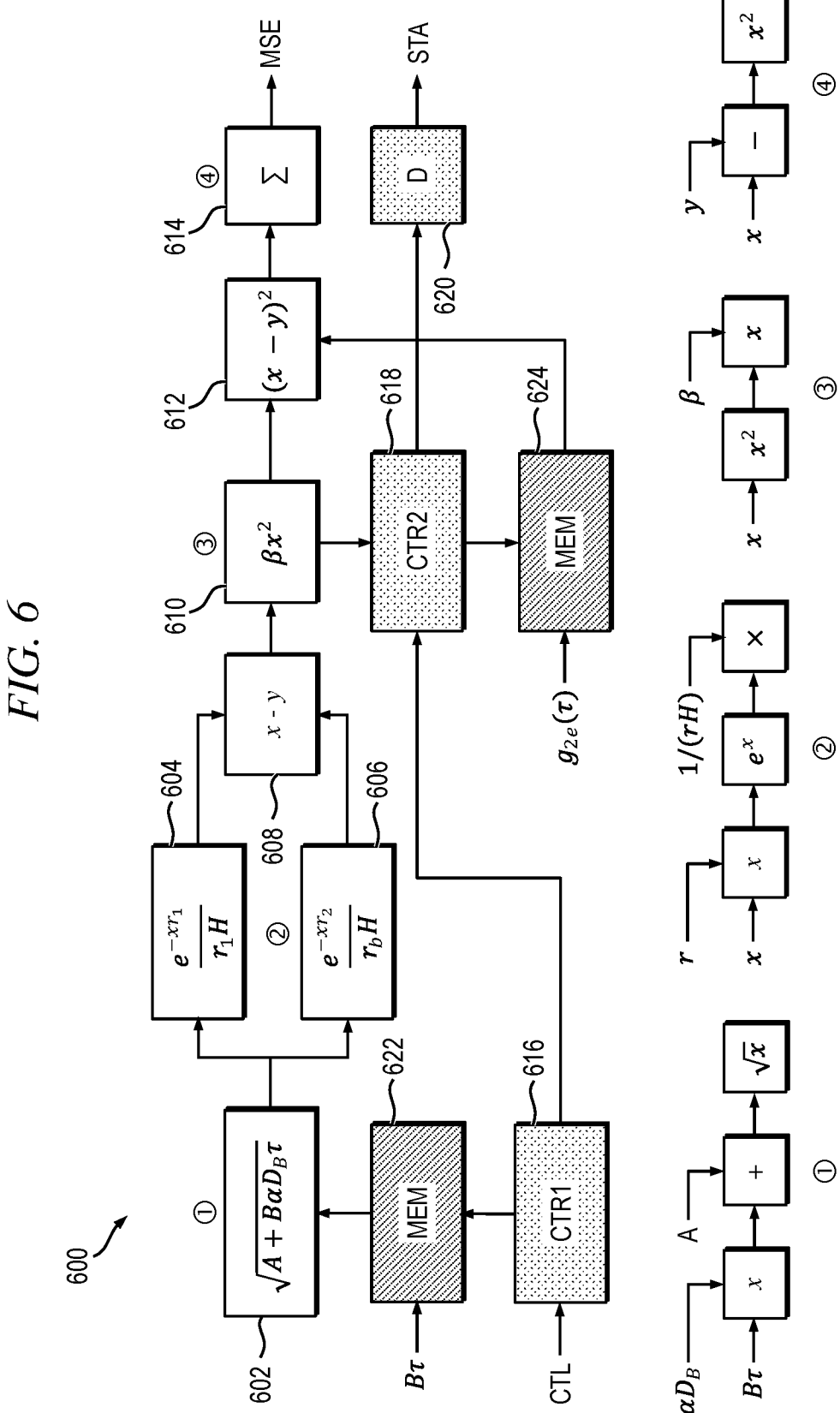
FIG. 6 is a block diagram depicting at least a portion of an example pipeline implementation for performing an MSE calculation in the DCS analyzer, according to one or more embodiments of the present invention.

The MSE module 502 using equations (2) and (3) is composed of the most complicated pipeline in the DCS analyzer, including computational blocks 602, 604, 606, 608, 610, 612 and 614, as will be described in further detail with reference to FIG. 6. More particularly, FIG. 6 is a block diagram depicting at least a portion of an example pipeline implementation 600 for performing the MSE calculation in the DCS analyzer, in accordance with one or more embodiments of the invention. The MSE module 600 includes a plurality of IP cores, including computational blocks 602, 604, 606, 608, 610 and 612, or modular combinations of IP cores (①, ②, ③, and ④). Each of these IP cores 602-612 is adapted to perform a specific computational stage in the MSE calculation. For example, block 602 is configured to iteratively calculate the term $\sqrt{A+B\alpha D_B \tau}$ in equation (2), blocks 604 and 606 are configured to calculate the terms $$\frac{e^{-xr_1}}{r_1 H}$$

and $$\frac{e^{-xr_2}}{r_b H},$$

respectively, in equation (2), block 608 is configured to perform a subtraction function of the form x−y, block 610 is configured to iteratively calculate the term $\beta x^2$ in equation (2), and block 612 is configured to perform a square function of the form $(x-y)^2$ in equation (3). Block 614 is an accumulator core configured to perform a summation function. Blocks 616 and 618 are counters, used for controlling the iteration, with $\alpha D_B$ and $\beta$ being iteration parameters. Block 620 is a delay unit of three clock cycles which turns the counter overflow signal generated by counter 618 into the STA output signal of the MSE module 600. Blocks 622 and 624 are memory used for storing the correlation delay and experiment data, or other intermediate values used throughout the MSE calculation. The inputs to the MSE module 600 are the acquired correlation data B$\tau$ and $g_{2e}(\tau)$, and x and y represent input data of the cores. Constants A, $r_1$, $r_b$ and H are stored in the FPGA memory.

The two terms inside the parenthesis in equation (2) are identical operations and therefore two instances of the same module ② are used in parallel to thereby beneficially improve processing throughput. The latencies of the computing cores in the module 600 are set to one FPGA clock cycle except for the square root core 602 in ① and exponent core 610 in ③. The square root core 602 has the latency of four FPGA clock cycles and the exponent core 610 has the latency of ten FPGA clock cycles, in this example embodiment. Based on those settings, module ① has a latency of six FPGA clock cycles, module ② has a latency of 13 FPGA clock cycles including the following subtraction, module ③ has a latency of two FPGA clock cycles, and module ④ has a latency of three FPGA clock cycles including the following accumulator core 614. Thus, the entire module 600 has a latency of 24 FPGA clock cycles.

Counters 616 and 618 (CTR1 and CTR2, respectively) are incremental counters driven by the FPGA clock, and the number of correlation time values N is their overflow values. The control module (e.g., control logic 510 in FIG. 5) resets both counters 616, 618 to zero as the initial addresses of the two memory blocks 622 and 624 holding the input data through the CTL signal from the control bus. The control module also starts the module 600 by enabling counter 616 to read the correlation data B$\tau$, and sends them to module ① one value per clock. The output data of module ① are the theoretical correlation values from the numerical model. Counter 618 is not enabled until a valid signal from module ③ is active. This synchronizes the theoretical correlation values with the acquired correlation values at the same time delay for the following MSE computation.

When counter 616 overflows, the valid signal to module ① becomes inactive indicating the end of data input to the module 600. When counter 618 reaches the overflow value, the overflow signal enters the delay unit 620 with the latency of three FPGA clock cycles, which is the total latency of the module ④ and the accumulation core 614. The output of the delay unit 620 is the active completion signal STA and ensures that the output MSE including the sum of squared errors of all data points. Since N is a constant during the curve fitting, there is no need to divide the MSE by N for the subsequent sorting step. When the control module receives the STA signal from the MSE module 600, it deactivates the CTL signal to put the MSE module on hold.

Figure 7:
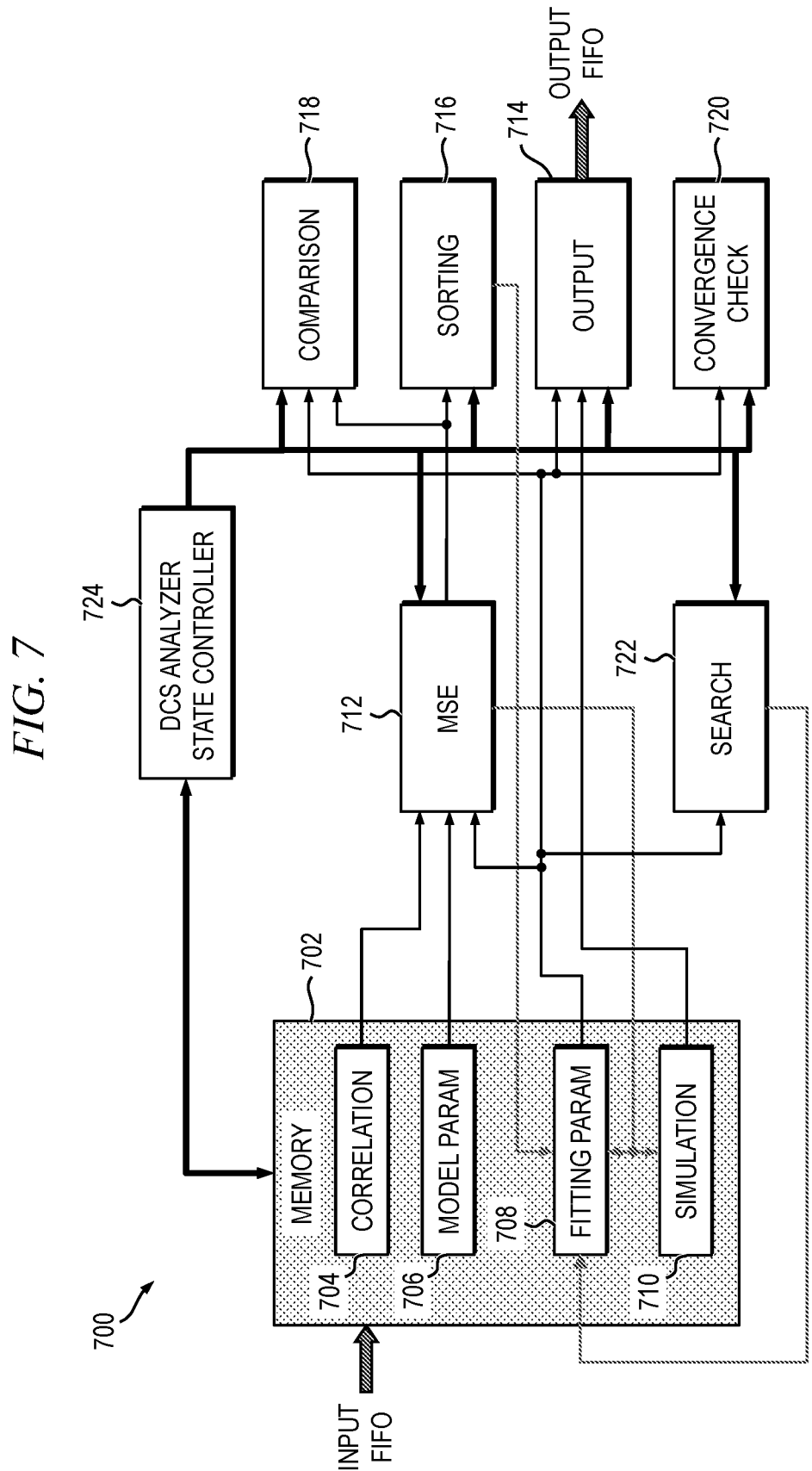
FIG. 7 is a block diagram depicting at least a portion of an example DCS analyzer, according to one or more alternative embodiments of the present invention.

With reference now to FIG. 7, a block diagram depicts at least a portion of an example DCS analyzer 700, according to an alternative embodiment of the invention. Like the DSC analyzer 500 shown in FIG. 5, by changing one or more parameters to the analyzer, the DCS analyzer 700 can implement both semi-infinite and infinite medium model solutions to the correlation diffusion equation for deriving the BFI.

More particularly, the DCS analyzer 700 includes a memory 702 for storing several parameters and/or intermediate results of the correlation diffusion equation solution. In one or more embodiments, the memory 702 includes a correlation unit 704, a model parameter unit 706, a fitting parameter unit 708 and a simulation unit 710. The correlation unit 704 is configured to store autocorrelation values of the scattered light (also called G2) from the correlator and related modified delay time values ($\tau_n$) used by an MSE module 712 included in the DCS analyzer 700. The MSE module 712 may be implemented in a manner consistent with the illustrative MSE module 600 shown in FIG. 6, except that MSE module 712 preferably includes a bypass switch so that no computation is needed if the MSE value is current.

The model parameter unit 706 stores model parameters used by the MSE module 712. In one or more embodiments, six model parameters are stored in the model parameter unit 708, including $-r1$, $-r2$, $tr1$, $tr2$, $(k_0)^2$, and $\alpha$ (the relative error for MSE). The fitting parameters unit 708 stores three sets of $\alpha D_B$, $\beta$, MSE and MSE flag data. If the MSE flag is true, the current MSE was computed from the current $\alpha D_B$ and $\beta$, and there is no need to compute again. The fitting parameters unit also stores indexes to the biggest (worst) MSE, medium (good) MSE and smallest (best) MSE values. The simulation unit 710 stores simulated correlation values obtain using the theoretical model; these values are called simulated G2 values.

The MSE module 712 in the DCS analyzer 700 computes the mean square error between the theoretical autocorrelation computed from the model parameters 706 and the measured autocorrelation. Input data to the MSE module 712 include correlation 704, model parameters 706 and fitting parameters 708. If the MSE flag stored in the fitting parameters unit 708 is true, the current MSE in the fitting parameters unit is output directly. Otherwise, a new MSE is computed. The MSE module 712 updates the MSE in the fitting parameters unit 708 and sets the MSE flag true. The output of the MSE module 712 is also sent to a sorting module 716 and a comparison module 718, the operation of which will be described in further detail below in conjunction with FIG. 8.

The sorting module 716 is configured to sort the latest three MSE values obtained from the MSE module 712 and produces indexes of the largest (worst), medium, and smallest (best) MSE values and their associated $\alpha D_B$ and $\beta$ values simultaneously. Indexes are stored in the fitting parameters unit 708. The comparison module 718 compares the latest (i.e., most recent) two MSE values. The comparison uses the expression $MSE_{current} < MSE_{previous}$, where $MSE_{current}$ is the current MSE value and $MSE_{previous}$ is the next previous MSE value, respectively.

The DCS analyzer 700 further includes a convergence checking module 720. The convergence checking module 720 is configured to check whether an absolute value of $(MSE_{largest} - MSE_{smallest})/MSE_{smallest}$ is lower than a prescribed threshold a. If so, convergence is reached. The convergence checking module also includes an iteration counter to prevent a non-convergence condition. In one or more embodiments, the iteration count value is set to 200, although embodiments of the invention are not limited to any specific value. Based on experimental results, the typical number of iterations before convergence is less than 100.

A search module 722 included in the DCS analyzer 700 is configured to calculate the $\alpha D_B$ and $\beta$ values at reflection, extension, contraction and shrink locations. All or at least a subset of computations are performed in parallel, thereby significantly improving processing speed, in accordance with aspects of the invention. The search module 722 employs the following equations. In the equations, it is assumed that X, Y and Z are the $\alpha D_B$ values associated with the smallest, medium, and largest MSEs, respectively.

Reflection value $R=X+Y-Z$

Extension value $E=2R-(X-Y)/2$

Contraction value $C=(X+Y)/4+Z/2$

Shrink value $SY=(X+Y)/2$

Shrink value $SZ=(X+Z)/2$

The same operations are performed on the $\beta$ values. The $\alpha D_B$ and $\beta$ values at those locations are selected and the corresponding MSE values are computed using the MSE module 712 based on the results of the comparison module 718. The $\alpha D_B$ and $\beta$ values and the corresponding MSE values are stored in registers in the search module.

The comparison module 718 compares the latest two MSE values. As previously stated, the comparison expression is $MSE_{current} < MSE_{previous}$. Using the above notations as MSE subscripts, the first two MSE values are $MSE_X$ and $MSE_R$. In this configuration, $MSE_X$ is the largest MSE and is sent to the comparison module first. $MSE_R$ is the MSE at the reflection point and is sent to the comparison module second. The comparison will be $MSE_R < MSE_X$. The next input is determined by the outcome of the comparison.

Figure 8:
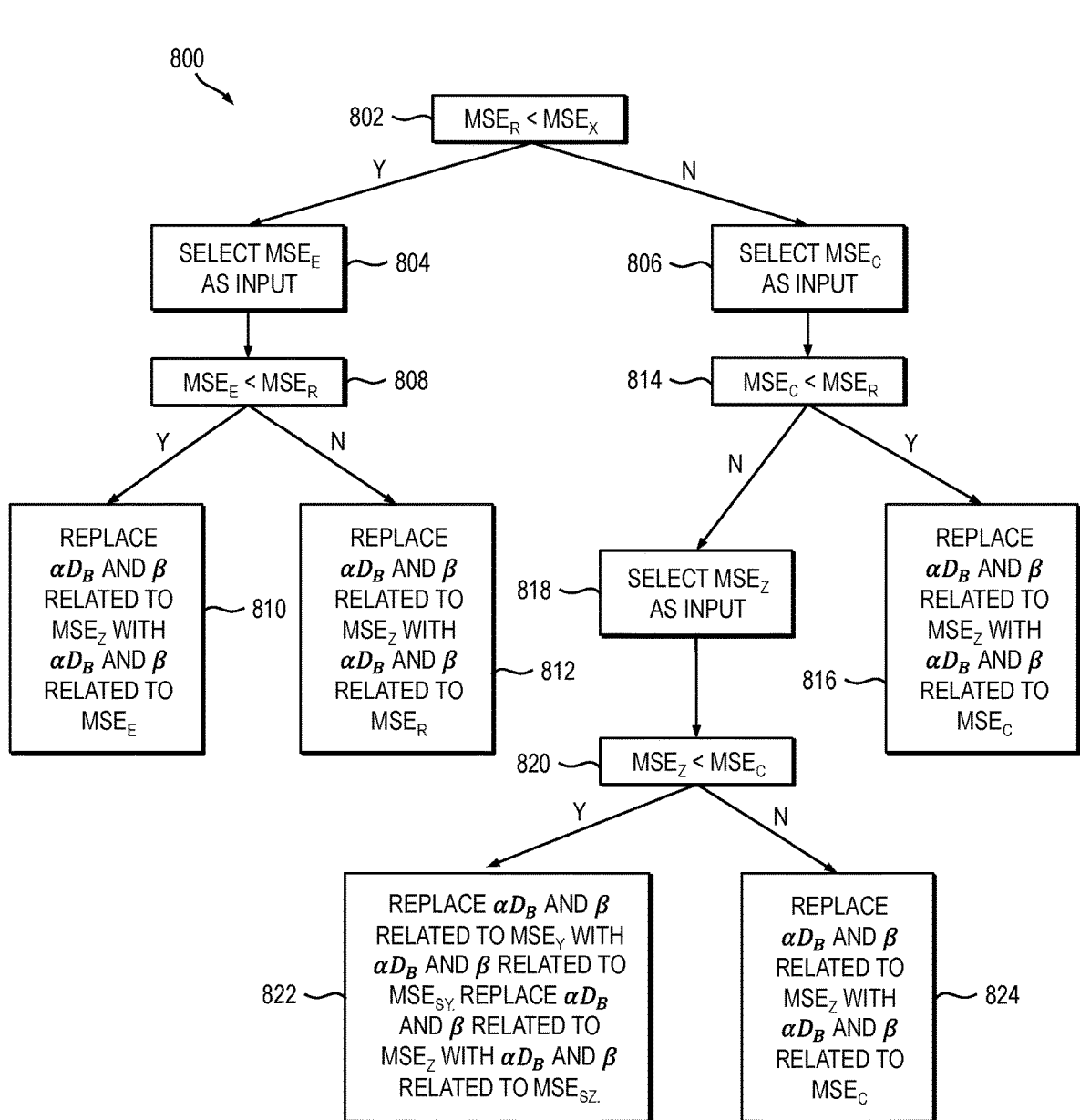
FIG. 8 is a flow diagram depicting at least a portion of an example method performed by an illustrative comparison module, according to one or more embodiments of the present invention.

FIG. 8 is a flow diagram depicting at least a portion of an example method performed by an illustrative comparison module (e.g., comparison module 718 shown in FIG. 7), according to one or more embodiments of the invention. The objective of the method 800 is to find the new $\alpha D_B$ and $\beta$ values to replace those with the largest (i.e., worst) MSE.

With reference now to FIG. 8, in step 802 a comparison is made between the values $MSE_R$ and $MSE_X$ to determine whether $MSE_R$ is less than $MSE_X$. If $MSE_R$ is less than $MSE_X$, as determined in step 802, the method 800 selects $MSE_E$ as the input in step 804. Otherwise, if $MSE_R$ is not less than $MSE_X$, the method 800 computes $MSE_C$ as the input in step 806.

With $MSE_E$ selected as the input in step 804, a comparison is made between the values $MSE_R$ and $MSE_E$ in step 808. If it is determined in step 808 that $MSE_E$ is less than $MSE_R$, the $\alpha D_B$ and $\beta$ values related to $MSE_Z$ are replaced with the $\alpha D_B$ and $\beta$ values related to $MSE_E$ in step 810. Otherwise, the $\alpha D_B$ and $\beta$ values related to $MSE_Z$ are replaced with the $\alpha D_B$ and $\beta$ values related to $MSE_R$ in step 812.

Similarly, after selecting $MSE_C$ as the input in step 806, a comparison is made between the values $MSE_R$ and $MSE_C$ in step 814. If it is determined in step 814 that $MSE_C$ is less than $MSE_R$, the $\alpha D_B$ and $\beta$ values related to $MSE_Z$ are replaced with the $\alpha D_B$ and $\beta$ values related to $MSE_C$ in step 816. Otherwise, the method 800 uses $MSE_Z$ as the input in step 818.

Using $MSE_Z$ as the input, as in step 818, a comparison is made between the values $MSE_Z$ and $MSE_C$ in step 820. If it is determined in step 820 that $MSE_Z$ is less than $MSE_C$, the $\alpha D_B$ and $\beta$ values related to $MSE_Y$ are replaced with the $\alpha D_B$ and $\beta$ values related to $MSE_{SY}$, and the $\alpha D_B$ and $\beta$ values related to $MSE_Z$ are replaced with the $\alpha D_B$ and $\beta$ values related to $MSE_{SZ}$ in step 822. Otherwise, if $MSE_Z$ is not less than $MSE_C$, as determined in step 820, the $\alpha D_B$ and $\beta$ values related to $MSE_Z$ are replaced with the $\alpha D_B$ and $\beta$ values related to $MSE_C$ in step 824.

Now referring again to FIG. 7, the DCS analyzer 700 further includes a DCS analyzer state controller 724, or other controller (e.g., microprocessor, etc.). The state controller 724 is configured to control an operation of the other modules in the DCS analyzer 700, including the memory 702, MSE module 712, output FIFO buffer 714, sorting module 716, comparison module 718, convergence check module 720, and search module 722. The state controller 724 is configured to make decisions based on the state feedback from each of these modules. By way of example only and without limitation, illustrative state descriptions and operations are described below.

Initialization State: This is the first state after powering up the DCS analyzer 700. The state controller 724 sets all control signals to an inactive state. It then enters an idle state.

Idle State: This is the state waiting for the command from the input FIFO. The state controller 724 maintains all control signals at the inactive state. There are two commands: Load command allows the input of data of autocorrelation values, DCS model parameters and initial $\alpha D_B$ and $\beta$ values; Run command starts the curve fitting of the DCS analyzer 700.

Load State: It is transitioned from the idle state when the load command is received. The state controller 724 sets the INPUTEN control signal active to enable the data input from the input FIFO and stores the respective data in the correlation 704, model parameters 706 and fitting parameters 708 portions in the memory 702. A Data Ready status signal is sent to the state controller 724 indicating the completion of the data input. It then returns to the idle state.

Run State: It is transitioned from the idle state when the run command is received. The state controller 724 sets MSECAL control signal active to compute the three MSEs from the three pairs of $\alpha D_B$ and $\beta$ values using the MSE module 712. The index to the fitting parameters, i.e. $\alpha D_B$, $\beta$, MSE and MSE flag, is set to zero. If the MSE flag is true, MSE computation is skipped and the MSE in the fitting parameters 708 is used as the output of the MSE module 712. At the end of each MSE computation, an active MSECalDone status signal is sent to the state controller 724 and the index is incremented by one. If the index is less than 3, continue the next MSE computation. If the index is greater than or equal to 3, it enters the sorting state. The output of MSE module 712 is sent to the sorting module 716, comparison module 718 and fitting parameters memory 708 with the MSE flag set as true. At this time, the sorting module has the latest three MSE values and the state is transitioned to the sorting state.

Sorting State: The state controller 724 sends a SORT-START control signal to the sorting module 716 and checks the MSESortDone status signal. When the signal is active, it enters the convergence state. This state determines the indexes of the largest, medium, and smallest MSE values and their associated $\alpha D_B$ and $\beta$ values. The state is then transitioned to the convergence state.

Convergence State: The state controller 724 sets a CNVSTART control signal active. It sends $MSE_{largest}$ and $MSE_{smallest}$ to the convergence module 720 to check convergences. An active ConvergeDone status signal indicates the completion of convergence check. A CNV status signal indicates the outcome of the check. Both status signals are sent to the state controller 724. If the CNV signal is active, convergence is reached, it enters the output state. Otherwise, it enters the search state. Another condition to end the iteration is the iteration counter reaching a prescribed iteration number and the state is transitioned to output state.

Search State: The state controller 724 sets a REFEXTCTR control signal active to compute the $\alpha D_B$ and $\beta$ values at the reflection, extension, contraction and shrink locations. The $\alpha D_B$ and $\beta$ values are selected to compute the MSE using the MSE module 712. The MSE is sent to the comparison module 718. The control signals involved are CMPSTART for the comparison module 718 and GMSE-SEL, MMSESEL and BMSESEL control signals the replacement of $\alpha D_B$ and $\beta$ values. A MSECmp status signal indicates the completion of the MSE comparison check. A CMP status signal indicates the outcome of the comparison. Both status signals are sent to the state controller 724. The CMP signal determines the next MSE sent to the comparison module 718 following the scheme depicted in FIG. 8 using REFEXTSEL and BMSECMP control signals. At the completion of the search, the state goes to run state for the next iteration.

Output State: The state controller 724 sets the DBOUTPU control signal active. The $\alpha D_B$ and $\beta$ values of the smallest MSE, MSE and the number of correlation values are output through the output FIFO. The state then transitions to the idle state.

As previously stated, in one or more illustrative embodiments, there are preferably six DCS model parameters: $-r1$, $-r2$, $tr1$, $tr2$, $(k_0)^2$, and $\alpha$ (the relative error for MSE). The choice of parameters can determine the particular DCS model used. Embodiments of the invention are suitable for use with a DCS semi-infinite model or a DCS infinite model.

For a DCS semi-infinite model, the following parameter definitions are assumed:

$$n_0 = 1.4$$

$$R = -1.44n_0^{-2} + 0.71n_0^{-1} + 0.668 + 0.0636n_0$$

$$k_0 = \frac{2\pi n_0}{\lambda}$$

$$lt = \frac{1}{\mu_s}$$

$$Ls = \frac{2(1-R)}{3\mu_s(1+R)}$$

$$kt = 6\mu_s^2 k_0^2$$

$$k_0 = \sqrt{3\mu_s\mu_a}$$

$$r_1 = \sqrt{\rho^2 + lt^2}$$

$$r_2 = \sqrt{\rho^2 + (lt + 2Ls)^2}$$

$$H = \frac{e^{-r_1 k_0}}{r_1} - \frac{e^{-r_2 k_0}}{r_2}$$

$$tr1 = \frac{1}{r_1 H}$$

$$tr2 = \frac{1}{r_2 H}$$

Modified time delay $$\tau_n = kt\tau = 6\mu_s^2 k_0^2 \tau$$

A theoretical equation of autocorrelation of the scattered light (G2) used in the DCS semi-infinite model is as follows:

$$G2 = \beta\left(\frac{e^{-r_1\sqrt{3\mu_s\mu_a + 6\mu_s^2 k_0^2 \alpha Db\tau}}}{Hr_1} - \frac{e^{-r_2\sqrt{3\mu_s\mu_a + 6\mu_s^2 k_0^2 \alpha Db\tau}}}{Hr_2}\right)^2$$

Similarly, for a DCS infinite model, the following parameter definitions are assumed:

$$n_0 = 1.4$$

18

-continued $$R = -1.44n_0^{-2} + 0.71n_0^{-1} + 0.668 + 0.0636n_0$$

$$k_0 = \frac{2\pi n_0}{\lambda}$$

$$kt = 6\mu_s^2 k_0^2$$

$$k_0 = \sqrt{3\mu_s\mu_a}$$

$$r_1 = \rho$$

$$r_2 = 0$$

$$F = e^{-r_1 k_0}$$

$$tr1 = \frac{1}{F}$$

$$tr2 = 0$$

Modified time delay $$\tau_n = kt\tau = 6\mu_s^2 k_0^2 \tau$$

A theoretical equation of autocorrelation of the scattered light (G2) used in the DCS infinite model is as follows:

$$G2 = \beta\left(\frac{e^{-r_1\sqrt{3\mu_s\mu_a + 6\mu_s^2 k_0^2 \alpha Db\tau}}}{F}\right)^2$$

Although only a single 8-channel correlator computing eight correlation values of consecutive time delays is shown and described herein, one skilled in the art will appreciate that multiple 8-channel correlators can be used in accordance with one or more embodiments of the invention for the computation of all correlation values. In a single-correlator embodiment, a memory is included which is configured to hold photon counts data. A single-correlator design has a benefit of using the minimum hardware resources to accommodate the scalable number of autocorrelation values at the output. An illustrative FPGA correlator uses multiples of an 8-channel correlator or similar structure to compute the autocorrelation. For example, if 128 autocorrelation values are required to be computed for different time delays, conventional correlators might require 16 8-channel correlators connected in a cascade fashion, which undesirably consumes significant resources. A single 8-channel correlator according to embodiments of the invention, however, does not need any change in configuration; one can easily modify the total number of iterations to produce the required result(s) in a more efficient manner.

Experimental Results

By way of example only and without limitation or loss of generality, an FPGA analyzer according to one or more embodiments of the invention was tested against a software analysis scheme in phantoms. Phantoms with a range of viscosities (and therefore effective diffusion constants DB) were produced utilizing glycerol, 20% Intralipid (Baxter Healthcare, Deerfield, IL), and water, following recipes from L. Cortese et al., "Liquid Phantoms for Near-Infrared and Diffuse Correlation Spectroscopies with Tunable Optical and Dynamic Properties," *Biomed. Opt. Express*, Vol. 9, No. 5, pp. 2068-2080 (2018), to maintain a constant $\mu'_s$. Four phantoms were produced with four different flow levels. The flow levels were measured using the DCS system with the novel FPGA analyzer and an independent DCS system with offline DCS analysis in a semi-infinite geometry for about five minutes for each phantom. BFI of the lowest viscosity phantom (no glycerol) was set as baseline. BFI is normalized to baseline using equation (5) below as the relative BFI (rBFI).

$$rBFI = \frac{BFT - BFI_{BASELINE}}{BFI_{BASELINE}} \quad (5)$$

The phantom test was conducted at room temperature (25 degrees Celsius). The rBFI of each phantom was measured by both DCS systems. A Bland Altman plot (see FIGS. 9A and 9B) was used to compare the consistency of the BFI measurement with 50 pairs of measurements for each phantom.

The DCS analyzer according to one or more embodiments was tested in an illustrative preclinical study of ischemia of spinal cord during spinal cord distraction in an adult sheep model. Details of the study will be reported separately. The protocol was approved by the IACUC at Stony Brook University. The sheep was pretreated with glycopyrrolate (0.02 mg/kg, IM). Anesthesia was induced with ketamine 10 to 20 mg/kg IM, animals were intubated, and anesthesia was maintained with isoflurane (1.5 to 3.0%). The spine was exposed sub-periosteally from T11 to L2. Fiber-optic probes were inserted into the epidural space through a laminotomy at the L1/L2 level and advanced to the planned distraction site under fluoroscopic imaging. Pedicle screws (5.5×30 mm) were placed at the lowest two thoracic levels and connected to 5.5 mm bilateral rods. Baseline flow data was obtained at the start of distraction and the spine was distracted at 2 mm intervals until a 50% drop in optically measured blood flow was observed or maximum distraction distance was reached. The DCS analyzer performed a real-time analysis of DCS data and presented the real-time rBFI.

Figure 9A:
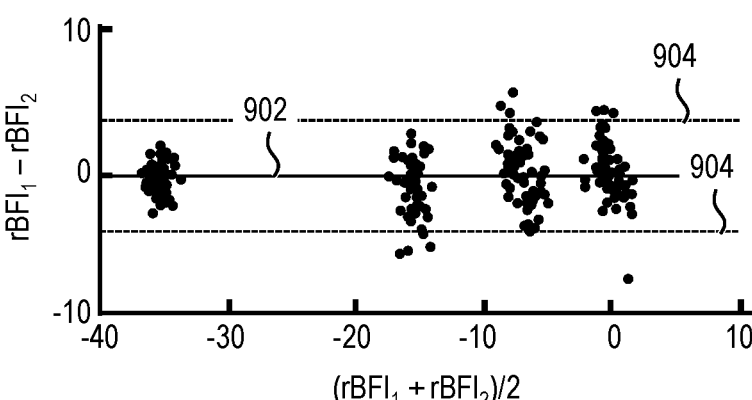
FIGS. 9A and 9B depict an example Bland Altman plot and a linear regression plot, respectively, comparing a difference between relative blood flow index (rBFI) measurements obtained from an FPGA DCS analyzer according to an embodiment of the present invention and from the BFI measured by conventional DCS using software analysis.
Figure 9B:
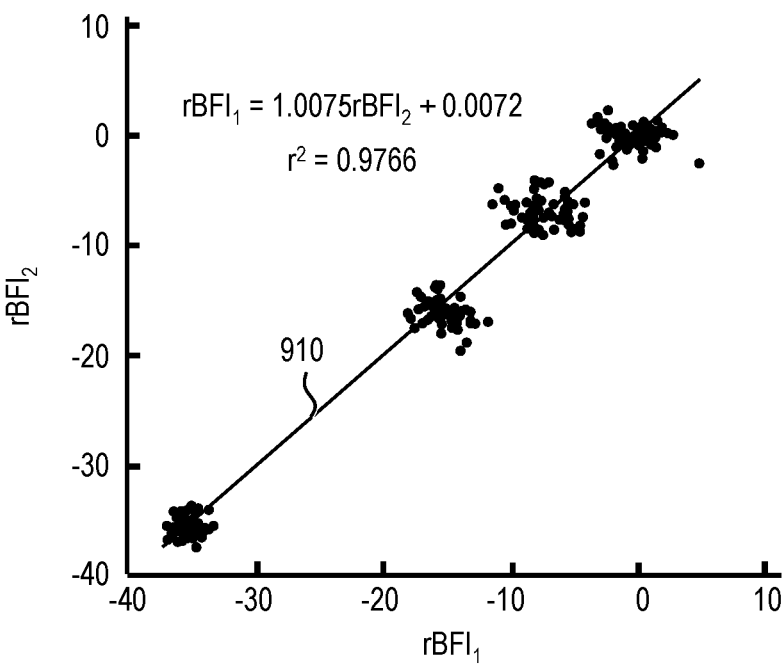

FIGS. 9A and 9B depict example Bland Altman plots comparing a difference between the rBFI measurements obtained from an FPGA analyzer according to an embodiment of the invention and rBFI measurements from software analysis; rBFI₁ is from the FPGA analyzer and rBFI₂ is from the software analysis. With reference to FIG. 9A, a Bland Altman plot depicts BFI measurements on four phantoms by two independent DCS systems. Solid line 902 indicates a difference mean and the two dotted lines 904 define a 95% confidence interval (1.96 standard deviation of the rBFI difference) from the difference mean. FIG. 9B depicts the linear correlation between the two rBFI measurements. Solid line 910 represents the case rBFI₁=rBFI₂.

As evidenced by the Bland Altman plot in FIG. 9A, the rBFI differences between the measurements obtained by the novel FPGA-based analyzer and those obtained by the software analysis are within a 95% confidence level. This suggests that both measurements were consistent. The linear correlation shown in FIG. 9B shows a high correlation with an r² value of about 98% and a slope of 1.01.

By way of illustration only and without limitation, the performance of the hardware (FPGA) implementation of the Nelder-Mead method was compared with the software approach to fit the measured autocorrelation function to the theoretical model. A counter was added in the FPGA to measure the total number of clocks used for the curve fitting of one data set. The computation time of the FPGA was the product of the total number of clocks and the FPGA clock cycle, which in this example was 25 ns at an FPGA frequency of 40 MHz. In addition to the FPGA-based algorithm, the MATLAB® (a registered trademark of Mathworks, Natick, MA) function fminsearch was utilized, which also uses the Nelder-Mead algorithm, to derive the BFI from the same correlation data. The MATLAB® profiling tool was used to measure the CPU time for the fminsearch function to process the same data set.

The MATLAB® code was executed on a Dell OptiPlex 9010 (Dell Technologies, Round Rock, TX) with a CPU of i7-3770 quad cores running at 3.4 GHz. Twenty-seven autocorrelation curves, each curve containing approximately 60 paired values of $\tau$ and $g_2$, were used in the test. The FPGA implementation used a single-precision float point as the data representation. The initial values of $\alpha D_B$ and $\beta$ were set the same for both the hardware (FPGA) and software (MATLAB®) computations. The averaged processing time was 539±127 µs for the FPGA processing and 51±8 ms for the fminseach function of MATLAB®. The BFI values of the same correlation data set from both methods were also compared. The relative error, defined as a ratio of the absolute difference between the FPGA BFI and the software BFI to the software BFI, is within 0.1%. This difference could be attributed to the data precision and the convergence criteria used in the two methods, among other factors.

Figure 10A:
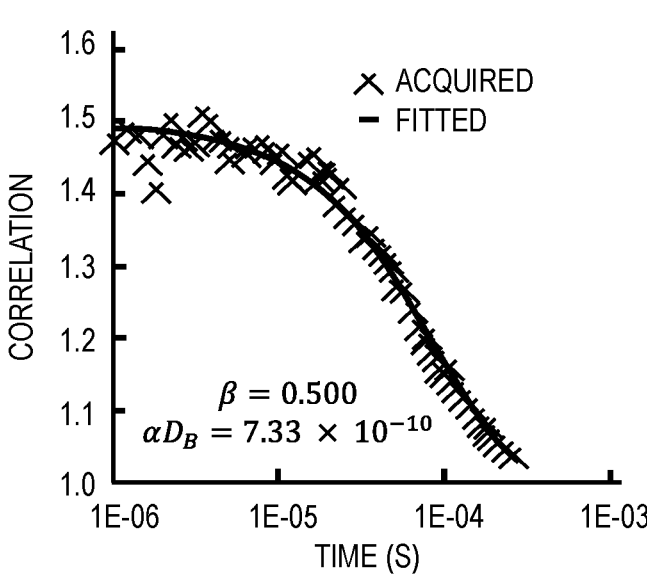
FIGS. 10A-10D depict four illustrative correlation fitting curves from an FPGA-based DCS analyzer according to one or more embodiments of the present invention.
Figure 10B:
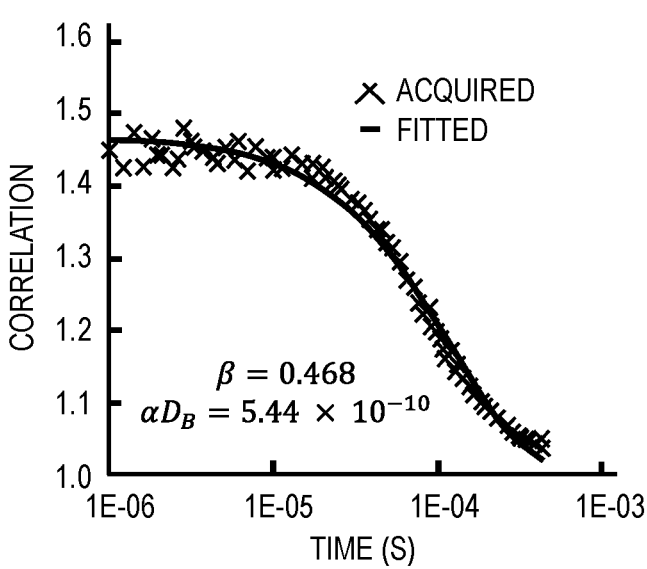
Figure 10C:
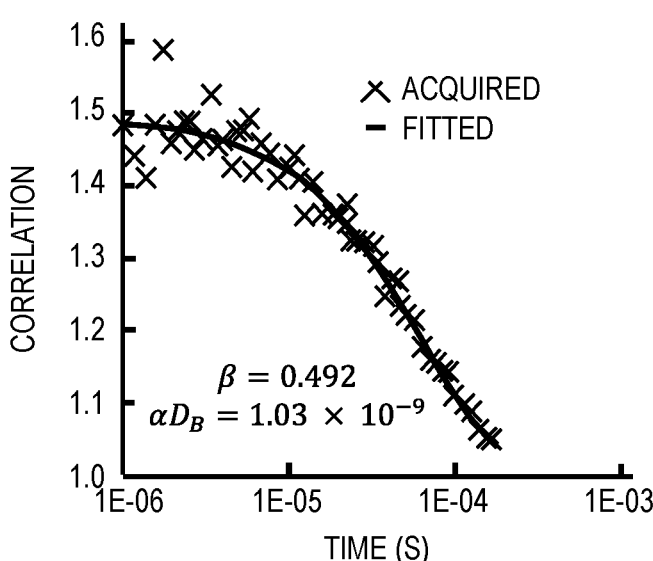
Figure 10D:
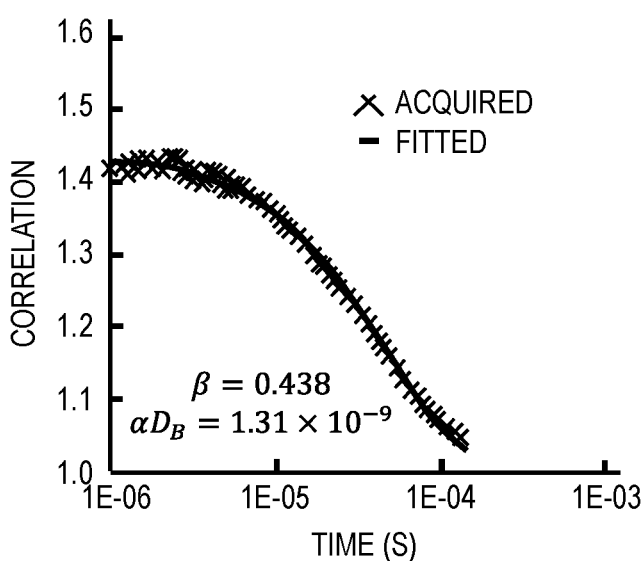

This DCS analysis system was utilized in a large-animal preclinical monitor of spinal cord ischemia to demonstrate the potential utility of real-time DCS analysis. FIGS. 10A-10D show four correlation fitting curves from the FPGA-based DCS analyzer according to one or more embodiments of the invention. Data were from two detectors acquired at the beginning of the stretch (baseline) and the end of stretch in the animal study. FIGS. 10A and 10B show the measurements at the distraction site; FIG. 10A is measured before the distraction and FIG. 10B is measured at the end of the distraction. FIGS. 10C and 10D show the measurements above the distraction site; FIG. 10C is measured before the distraction and FIG. 10D is measured at the end of the distraction. FIGS. 10A-10D demonstrate the fitting quality of the hardware FPGA analyzer under these different scenarios. Specifically, FIG. 10A depicts fitted versus acquired correlation at the distraction site (i.e., the location where the spinal cord is pulled) at the beginning of the stretch (baseline), FIG. 10B depicts fitted versus acquired correlation at the distraction site at the end of the stretch, FIG. 10C depicts fitted versus acquired correlation above the distraction site (i.e., at a location between the head and the distraction site) at the beginning of the stretch (baseline), and FIG. 10D depicts fitted versus acquired correlation above the distraction site at the end of the stretch.

Figure 11:
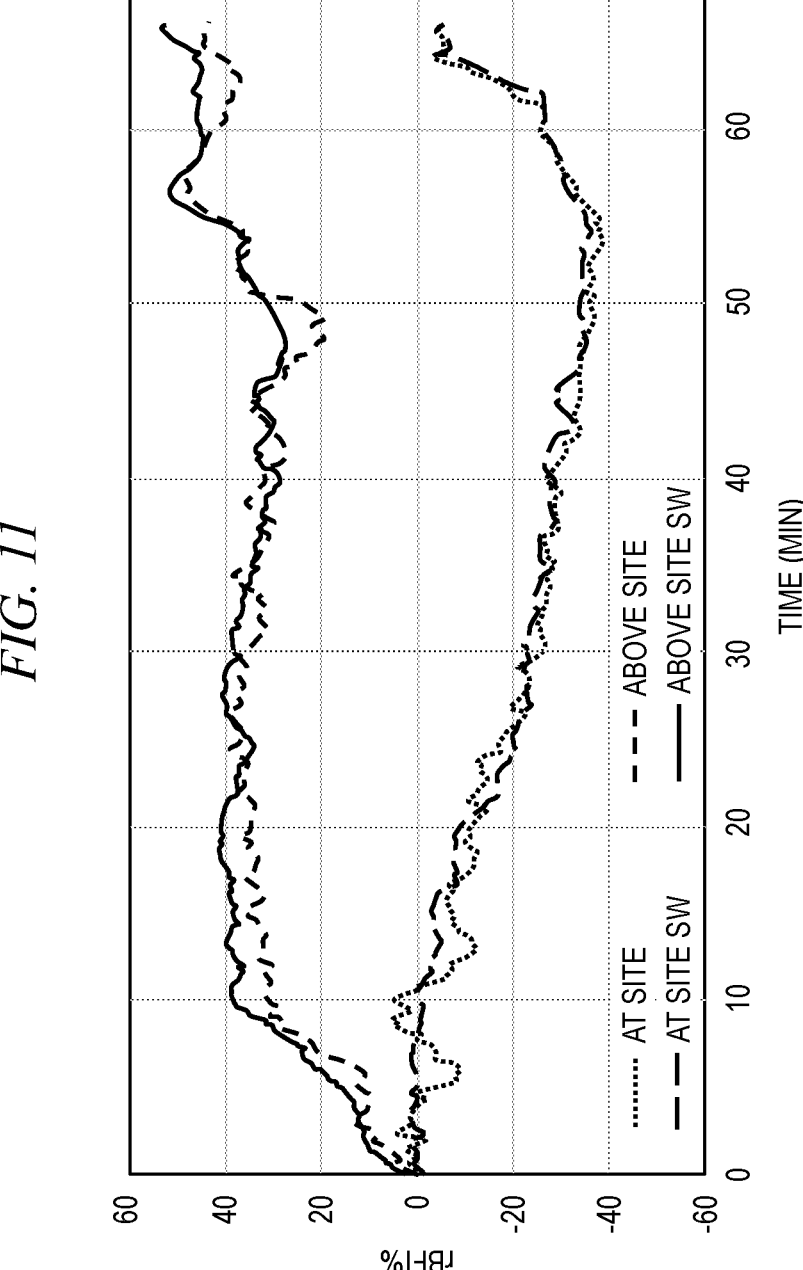
FIG. 11 demonstrates an illustrative time course, showing rBFI versus time duration at and above the distraction levels during an in vivo spinal cord distraction animal experiment, according to one or more embodiments of the present invention.

FIG. 11 demonstrates an illustrative time course, showing rBFI percentage at and above the distraction levels, according to one or more embodiments of the invention. As apparent from FIG. 11, flow falls at the site of distraction and increases above the distraction site. The distraction started at 0 minutes, defining a baseline BFI for each site. The rBFI at the distraction site decreased progressively with increasing distraction to a nadir of about −40% of baseline at 54 minutes. Following release of the distraction hardware at around 56 minutes, blood flow at the site of injury recovered slowly to nearly the baseline level. During this period, rBFI at the site superior to the distraction site continue to increase up to about 50%. This increase in blood flow may be due to a redirection of blood flow from the distraction site into alternate paths in the spinal cord vasculature.

The results of the full parametric fit were displayed in the operating room, enabling clinicians to observe the change of spinal cord blood flow in real-time throughout the surgery. The correlation data from animal study were also processed by MATLAB® DCS analysis software offline for the system level comparison and both results matched well. The minor difference between the hardware (FPGA) data and the software DSC analysis data could be attributed to the difference in the preprocessing of the correlation data and the post-processing of the BFI data in the two methods.

It is computationally intensive to obtain the BFI from measured autocorrelation of the scattering lights from tissue using the analytical DCS model. Curve fitting of the measured autocorrelation values with the theoretical model is a nonlinear process which requires the repeated computation of the theoretical correlation values from the pair of $\alpha D_B$ (BFI) and $\beta$ parameters in the model until convergence. That process is time consuming and must be repeated for each time point and detector channel. Existing real-time fitting algorithms in software frequently use a simplified fitting procedure, for example, calculating the half time of the decay, to minimize the computational load.

The DCS analysis algorithm of non-linear fitting was successfully implemented in hardware on an FPGA chip, in accordance with aspects of the invention. Although not limited by the choice of optimization algorithms, the Nelder-Mead method, used to find the minimum or maximum of an objective function in a multidimensional space, was adopted in the example embodiment described herein primarily because it involves only simple math computations implementable in the FPGA. The phantom study demonstrated that the DCS system with the hardware analyzer produced consistent data compared to the independent DCS system requiring offline DCS data analysis. The pre-clinical study has proven that the hardware-implemented DCS analyzer according to embodiments of the invention beneficially enables real-time processing of DCS data and the presentation of rBFI to clinicians intraoperatively.

Conventional DCS systems rely on powerful desktop computers for DCS data processing, or post-processing (offline) of BFI data. Although it may be known to use hardware correlators to relieve the computation burden of the autocorrelation of the scattered light from the main computer, a high-end desktop computer is required to provide the computational power for performing DCS analysis to obtain the BFI. However, this approach is not suitable for applications in which portability and/or size of the DCS device is crucial.

The hardware-based (FPGA) DCS analyzer according to embodiments of the present invention advantageously moves the computational burden of the DCS algorithm to the FPGA hardware. This superior approach provides real-time processing capability and significantly reduces the required computing power, thereby minimizing the DCS device profile and enabling the use of computers with limited capacity (e.g., tablets and other mobile devices) for user interface, device control and data presentation. Furthermore, embodiments of the invention allow the DCS device to be integrated with multi-device clinical monitors.

A DCS analyzer implemented in accordance with embodiments of the invention enable the DCS correlator and analyzer to be integrated into the same FPGA chip, thus providing a complete device-on-a-chip solution for DCS data processing. The FPGA chip configured according to aspects of the invention will accept the output from the photo detector, compute the correlation of the scattered light intensity, and derive the BFI as an output in real-time. When combined with microcontroller technology, the FPGA chip can communicate with the computing device through a variety of wired or wireless communication links and make the DCS system highly portable, with fast real-time processing capability.

The DCS FPGA analyzer provided a full parametric fit of the DCS theoretical model. It can also be adapted to process correlation curves calculated from photons binned by detector arrival time; i.e. time-domain DCS. In one or more embodiments, the DCS analyzer implementation utilizes a semi-infinite model. This design is modular: multiple analyzer modules can be implemented on one FPGA chip. An example DCS analyzer implementation according to some embodiments of the invention used 12.5% of the total available CLBs, 2.5% of block RAM and 8% of DSP units on a Xilinx Kintex 325 FPGA for one channel. This usage represents about ⅛ of the overall chip capacity, suggesting that at least 6 detector channels may be analyzed with the same FPGA chip.

Preliminary performance tests showed that the DCS FPGA analyzer according to one or more embodiments of the invention is at least comparable to a typical software solution. It takes less than about 1 ms to finish one curve fitting on an FPGA and enables real-time data display, even for "fast" DCS data collected at about 100 Hz. Two main factors affect the performance difference between FPGA and CPU. First, the software runs under the support of an operating system and must compete for resources with other software threads running on the CPU. The CPU time spent on the DCS analysis is dependent on the number of concurring threads and their priorities. Even though the CPU is running at GHz frequencies, the effective running speed of the DCS analysis is much lower. By comparison, the FPGA solution according to embodiments of the invention is implemented in a digital circuit entirely dedicated to the DCS analysis algorithm and operating at the full speed of the FPGA clock. Second, the software solution processes data in serial. For example, the correlation from the theoretic model is computed one value at a time. That means that the next correlation value will not be processed until the completion of the current correlation value. The FPGA solution according to embodiments of the invention uses a pipeline for parallel processing so that the computation of the correlation values are handled one value per FPGA clock cycle. In an example FPGA implementation, the pipeline takes 21 FPGA clock cycles out of 24 clock cycles in the MSE module to compute one correlation value. However, during the 21 FPGA clocks, there are 20 other correlation values are being concurrently calculated in the pipeline. This pipeline architecture is highly efficient in terms of resources used and is scalable to accommodate any data size without the need for additional computation units.

By way of example only and without limitation, in an illustrative embodiment of the DCS analyzer, the pipeline for the computation of one MSE has a latency of 24 clock cycles. To compute an MSE from equation (2) above and a measured autocorrelation function of 50 time delays (values of $\tau$), it takes 73 FPGA clock cycles (49+24). If the same computation is done in serial processing, as performed in a software DSC analysis, it will take 1200 clock cycles (50*24) for the same data size. This performance advantage of the hardware-based DCS analyzer will be even greater with increasing data sizes (number of $\tau$ values). In the DCS analysis, the time savings is significant using the FPGA pipeline solution at least because most of the processing time is spent on the repeated computation of the theoretical correlation values in the curve-fitting algorithm.

At least a portion of the techniques of the present invention may be implemented in an integrated circuit. In forming integrated circuits, identical die are typically fabricated in a repeated pattern on a surface of a semiconductor wafer. Each die includes a device described herein, and may include other structures or circuits. The individual die are cut or diced from the wafer, then packaged as an integrated circuit. One skilled in the art would know how to dice wafers and package die to produce integrated circuits. Any of the example structures or circuits illustrated in the accompanying figures, or portions thereof, may be part of an integrated circuit. Integrated circuits so manufactured are considered part of this invention.

Those skilled in the art will appreciate that the example structures discussed above can be distributed in raw form (i.e., a single wafer having multiple unpackaged chips), as bare dies, in packaged form, or incorporated as parts of intermediate products or end products that benefit from having a DCS analyzer and/or DCS correlator formed therein in accordance with one or more embodiments of the invention, such as, for example, an embedded hardware DCS system.

An integrated circuit in accordance with aspects of the present disclosure can be employed in essentially any DCS application and/or electronic system, particularly DCS systems requiring real-time processing capability and/or portability. Systems incorporating such integrated circuits are considered part of this invention. Given the teachings of the present disclosure provided herein, one of ordinary skill in the art will be able to contemplate other implementations and applications of embodiments of the invention.

The illustrations of embodiments of the invention described herein are intended to provide a general understanding of the various embodiments and are not intended to serve as a complete description of all the elements and features of apparatus and systems that might make use of the module, circuits and/or methods described herein. Many other embodiments will become apparent to those skilled in the art given the teachings herein; other embodiments are utilized and derived therefrom, such that structural and logical substitutions and changes can be made without departing from the scope of this disclosure. The drawings are also merely representational and are not drawn to scale. Accordingly, the specification and drawings are to be regarded in an illustrative rather than a restrictive sense.

Embodiments of the invention are referred to herein, individually and/or collectively, by the term "embodiment" merely for convenience and without intending to limit the scope of this application to any single embodiment or inventive concept if more than one is, in fact, shown. Thus, although specific embodiments have been illustrated and described herein, it should be understood that an arrangement achieving the same purpose can be substituted for the specific embodiment(s) shown; that is, this disclosure is intended to cover any and all adaptations or variations of various embodiments. Combinations of the above embodiments, and other embodiments not specifically described herein, will become apparent to those of skill in the art given the teachings herein.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes," and/or "including" specify the presence of stated features, steps, operations, elements, and/or components, but do not preclude the presence or addition of one or more other features, steps, operations, elements, components, and/or groups thereof. Terms such as "above" and "below" are used to indicate relative positioning of elements or structures to each other as opposed to relative elevation.

The corresponding structures, materials, acts, and equivalents of all means or step-plus-function elements in the claims below are intended to include any structure, material, or act for performing the function in combination with other claimed elements as specifically claimed. The description of the various embodiments has been presented for purposes of illustration and description, but is not intended to be exhaustive or limited to the forms disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the various embodiments with various modifications as are suited to the particular use contemplated.

The abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the appended claims reflect, inventive subject matter lies in less than all features of a single embodiment. Thus, the following claims are hereby incorporated into the Detailed Description, with each claim standing on its own as separately claimed subject matter.

Given the teachings of embodiments of the invention provided herein, one of ordinary skill in the art will be able to contemplate other implementations and applications of the techniques of embodiments of the invention. Although illustrative embodiments of the invention have been described herein with reference to the accompanying drawings, it is to be understood that embodiments of the invention are not limited to those precise embodiments, and that various other changes and modifications are made therein by one skilled in the art without departing from the scope of the appended claims.

What is claimed is:

1. An embedded diffuse correlation spectroscopy (DCS) analyzer to measure blood perfusion in a biological tissue, the analyzer comprising:

a memory, the memory storing autocorrelation values, model parameters used in solving an autocorrelation equation of scattered light, fitting parameters, and simulated correlation values obtained from a theoretical DCS model, the scattered light being detected by a photodetector from the blood perfusion in the biological tissue;

a hardware mean square error (MSE) module, the MSE module configured to compute a mean square error between theoretical autocorrelation values computed from the model parameters and measured autocorrelation values;

a hardware sorting module, the sorting module configured to sort a latest three MSE values obtained from the MSE module and to generate indexes of largest, medium, and smallest MSE values, the indexes being stored in the memory as a subset of the fitting parameters;

a hardware convergence checking module configured to determine whether convergence is reached in solving the autocorrelation equation;

a hardware search module configured to calculate $\alpha D_B$ and $\beta$ values at reflection, extension, contraction, and shrink locations, the $\alpha D_B$ and $\beta$ values being calculated in parallel;

a hardware comparison module configured to compare two latest MSE values and to facilitate finding new $\alpha D_B$ and $\beta$ values to replace those values associated with a largest MSE;

a state controller coupled with the memory and modules comprising the MSE module, the sorting module, the convergence checking module, the search module, and the comparison module to control an operation thereof, and an output buffer configured to present, as an output of the DCS analyzer, a fitted solution of the autocorrelation equation, facilitating real-time quantification of the blood perfusion in the biological tissue.

2. The DCS analyzer according to claim 1, wherein the MSE module is configured to compute the MSE between a theoretical autocorrelation and a measured autocorrelation using a pipeline structure for parallel computing and high throughput.

3. The DCS analyzer according to claim 1, further comprising a first buffer coupled between the state controller and the MSE module, the first buffer being configured to send modified correlation values and corresponding modified delay time values ($\tau_n$), generated by the state controller, to the MSE module.

4. The DCS analyzer according to claim 3, further comprising a second buffer coupled between the memory and the state controller, the second buffer being configured to output $\alpha D_B$ and $\beta$ values of a smallest MSE to the state controller when prescribed convergence criteria are met.

5. The DCS analyzer according to claim 4, wherein at least one of the first buffer and second buffer is a first-in-first-out buffer.

6. The DCS analyzer according to claim 1, wherein data paths between the memory and at least one of the modules are bidirectional.

7. The DCS analyzer according to claim 1, wherein a start operation of at least one of the modules is controlled by one or more control signals asserted by the state controller.

8. The DCS analyzer according to claim 1, wherein the modules are configured to send end of operation and status signals to the state controller.

9. The DCS analyzer according to claim 1, wherein the state controller is configured to receive at least one command to load data from an input buffer and to store the data in the memory for DCS analysis.

10. The DCS analyzer according to claim 1, further comprising an input buffer, wherein the state controller is configured to receive at least one command from the input buffer to start DCS analysis.

11. The DCS analyzer according to claim 1, wherein the state controller is configured to switch operation states based on feedback from a status signal.

12. The DCS analyzer according to claim 1, wherein, based on feedback from the comparison module, the state controller is configured to:

select a smallest MSE value ($MSE_X$) as a first input and MSE at a reflection location ($MSR_R$) as a second input, determine whether $MSE_R$ is less than $MSE_X$;

select MSE at an extension location ($MSE_E$) as an input when $MSE_R$ is less than the current MSE value and determine whether $MSE_E$ is less than a current $MSE_R$;

replace $\alpha D_B$ and $\beta$ values related to a largest MSE value ($MSE_Z$) with $\alpha D_B$ and, $\beta$ values related to $MSE_E$ when $MSE_E$ is less than $MSE_R$;

replace $\alpha D_B$ and $\beta$ values related to $MSE_Z$ with $\alpha D_B$ and $\beta$ values related to $MSE_R$ when $MSE_E$ is not less than $MSE_R$, select MSE at a contraction location ($MSE_C$) as an input when $MSE_R$ is not less than $MSE_X$ and determine whether $MSE_C$ is less than a current $MSE_R$;

replace $\alpha D_B$ and $\beta$ values related to $MSE_Z$ with $\alpha D_B$ and $\beta$ values related to $MSE_C$ when $MSE_C$ is less than $MSE_R$;

select $MSE_Z$ as an input when $MSE_C$ is not less than $MSE_R$ and determine whether $MSE_Z$ is less than a $MSE_C$;

when $MSE_Z$ is less than $MSE_C$, replace $\alpha D_B$ and $\beta$ values related to a medium MSE value ($MSE_Y$) with $\alpha D_B$ and $\beta$ values related to MSE in a first shrink location ($MSE_{SY}$), and replace $\alpha D_B$ and $\beta$ values related to $MSE_Z$ with $\alpha D_R$ and $\beta$ values related to MSE in a second shrink location ($MSE_{SZ}$); and when $MSE_Z$ is not less than $MSE_C$, replace $\alpha D_B$ and $\beta$ values related to $MSE_Z$ with $\alpha F_B$ and $\beta$ values related to $MSE_C$.

13. The DCS analyzer according to claim 1, wherein the state controller is configured to start operation of at least one of the modules, control signals based on current states, and end of operation and status of at least one of the modules.

14. The DCS analyzer according to claim 1, further comprising an output buffer, wherein the state controller is configured to output data comprising at least one of $\alpha D_B$, $\beta$, MSE and a number of correlation values, through the output buffer.

15. The DCS analyzer according to claim 1, wherein the sorting module is configured to determine an order of three latest input MSE values and to generate corresponding indexes to large, medium, and small MSE values simultaneously.

16. The DCS analyzer according to claim 1, wherein the search module is configured to compute MSE $\alpha D_B$ and $\beta$ values at reflection, extension, construction, and shrink locations simultaneously, and to store results of the computation in the memory.

17. The DCS analyzer according to claim 1, wherein the convergence module is configured to check whether a relative change of a small MSE is within a prescribed limit, or whether a number of iterations has reached a prescribed limit, and to decide when to end a curve fitting iteration.

18. The DCS analyzer according to claim 1, wherein the DCS analyzer is implemented in a field-programmable gate array (FPGA).

19. An apparatus to perform diffuse correlation spectroscopy (DCS) to measure blood perfusion in a biological tissue, the apparatus comprising:

a hardware DCS correlator; and a hardware DCS analyzer coupled with the DCS correlator and embedded therewith on an integrated circuit chip, the DCS analyzer comprising:

a memory, the memory storing autocorrelation values, model parameters used in solving an autocorrelation equation of scattered light, fitting parameters, and simulated correlation values obtained from a theoretical DCS model, the scattered light being detected by a photodetector from the blood perfusion in the biological tissue;

a hardware mean square error (MSE) module configured to compute a mean square error between theoretical autocorrelation values computed from the model parameters and measured autocorrelation values;

a hardware sorting module configured to sort a latest three MSE values obtained from the MSE module and to generate indexes of largest, medium, and smallest MSE values, the indexes being stored in the memory as a subset of the fitting parameters;

a hardware convergence checking module configured to determine whether convergence is reached in solving the autocorrelation equation;

a hardware search module configured to calculate $\alpha D_B$ and $\beta$ values at reflection, extension, contraction, and shrink locations, the $\alpha D_B$ and $\beta$ values being calculated in parallel;

a hardware comparison module configured to compare two latest MSE values and facilitate finding new $\alpha D_B$ and $\beta$ values to replace those values associated with a largest MSE;

a state controller coupled with the memory and modules comprising the MSE module, the sorting module, the convergence checking module, the search module, and the comparison module to control an operation thereof; and an output buffer to present, as an output of the DCS analyzer, a fitted solution of the autocorrelation equation, facilitating real-time quantification of the blood perfusion in the biological tissue.

20. An embedded diffuse correlation spectroscopy (DCS) analyzer to measure blood perfusion in a biological tissue, the analyzer comprising:

a memory, the memory storing autocorrelation values, model parameters used in solving an autocorrelation equation of scattered light, fitting parameters, and simulated correlation values obtained from a theoretical DCS model, the scattered light being detected by a photodetector from the blood perfusion in the biological tissue;

a hardware mean square error (MSE) module configured to compute a mean square error between theoretical autocorrelation values computed from the model parameters and measured autocorrelation values;

a hardware sorting module configured to sort a latest three MSE values obtained from the MSE module and to generate indexes of largest, medium, and smallest MSE values, the indexes being stored in the memory as a subset of the fitting parameters;

a hardware convergence checking module configured to determine whether convergence is reached in solving the autocorrelation equation;

a hardware search module configured to calculate $\alpha D_R$ and $\beta$ values at reflection, extension, contraction, and shrink locations, the $\alpha D_B$ and $\beta$ values being calculated in parallel;

a hardware comparison module configured to compare two latest MSE values and to facilitate finding new $\alpha D_B$ and $\beta$ values to replace those values associated with a largest MSE;

a state controller coupled with the memory and modules comprising the MSE module, the sorting module, the convergence checking module, the search module, and the comparison module to control an operation thereof; and an output buffer configured to present, as an output of the DCS analyzer, a fitted solution of the autocorrelation equation, facilitating real-time quantification of the blood perfusion in the biological tissue, wherein based on feedback from the comparison module, the state controller is configured to:

select a smallest MSE value ($MSE_x$) as a first input and MSE at a reflection location ($MSR_R$) as a second input;

determine whether $MSE_R$ is less than $MSE_X$;

select MSE at an extension location ($MSE_E$) as an input when $MSE_R$ is less than the current MSE value and determine whether $MSE_E$ is less than a current $MSE_R$;

replace $\alpha D_B$ and $\beta$ values related to a largest MSE value ($MSE_Z$) with $\alpha D_B$ and $\beta$ values related to $MSE_E$ when $MSE_E$ is less than $MSE_R$;

replace $\alpha D_B$ and $\beta$ values related to $MSE_Z$ with $\alpha D_B$ and $\beta$ values related to $MSE_R$ when $MSE_E$ is not less than $MSE_R$;

select MSE at a contraction location ($MSE_C$) as an input when $MSE_R$ is not less than $MSE_X$ and determine whether $MSE_C$ is less than a current $MSE_R$;

replace $\alpha D_B$ and, $\beta$ values related to $MSE_Z$ with $\alpha D_B$ and, $\beta$ values related to $MSE_C$ when $MSE_C$ is less than $MSE_R$;

select $MSE_Z$ as an input when $MSE_C$ is not less than $MSE_R$ and determine whether $MSE_Z$ is less than a $MSE_C$;

when $MSE_Z$ is less than $MSE_C$, replace $\alpha D_B$ and $\beta$ values related to a medium MSE value ($MSE_Y$) with $\alpha D_B$ and $\beta$ values related to MSE in a first shrink location ($MSE_{SY}$), and replace $\alpha D_B$ and $\beta$ values related to $MSE_Z$ with $\alpha D_B$ and $\beta$ values related to MSE in a second shrink location ($MSE_{SZ}$); and when $MSE_Z$ is not less than $MSE_C$, replace $\alpha D_B$ and $\beta$ values related to $MSE_Z$ with $\alpha D_B$ and $\beta$ values related to $MSE_C$.

* * * * *